(12) United States Patent
Bishop

(10) Patent No.: US 10,329,615 B2
(45) Date of Patent: Jun. 25, 2019

(54) METHOD FOR REDUCING DEPHASING DURING CLUSTER DNA SEQUENCING

(71) Applicant: Thomas Frederick Bishop, Dunedin (NZ)

(72) Inventor: Thomas Frederick Bishop, Dunedin (NZ)

( * ) Notice: Subject to any disclaimer, the term of this patent is extended or adjusted under 35 U.S.C. 154(b) by 228 days.

(21) Appl. No.: 15/205,002

(22) Filed: Jul. 8, 2016

(65) Prior Publication Data

US 2017/0016064 A1 Jan. 19, 2017

Related U.S. Application Data

(60) Provisional application No. 62/189,801, filed on Jul. 8, 2015.

(51) Int. Cl.
 *C12Q 1/68* (2018.01)
 *C12Q 1/6874* (2018.01)
(52) U.S. Cl.
 CPC .................................. *C12Q 1/6874* (2013.01)

(58) Field of Classification Search
 None
 See application file for complete search history.

(56) References Cited

PUBLICATIONS

Shendure et al. (Current Protocols in Molecular Biology, 2011, 7.1.1-7.1.23) (Year: 2011).*

\* cited by examiner

*Primary Examiner* — Stephanie K Mummert

(57) ABSTRACT

A method for nucleic acid sequencing, comprising: exposing a plurality of clusters of a plurality of template polynucleotide strands to a series of flows of a plurality of nucleotide or oligonucleotide solutions, wherein the nucleotide solutions or oligonucleotide solutions are flowed in an order of flow which is not a continuous repeat of an ordering of a single flow of each of the nucleotide solutions or oligonucleotide solutions; and obtaining a fluorescence signal indicative of which, if any, nucleotide species or oligonucleotide species incorporated to determine a predicted sequence of nucleotides corresponding to the template polynucleotide strands. This method enables dephased amplicons to return in-phase.

28 Claims, 16 Drawing Sheets

Specification includes a Sequence Listing.

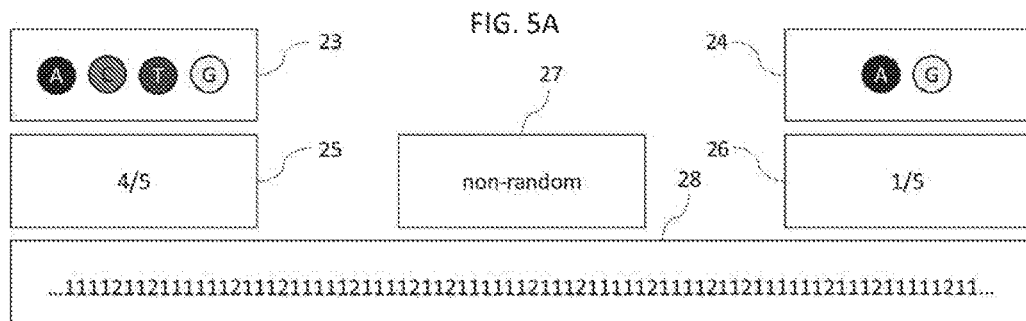
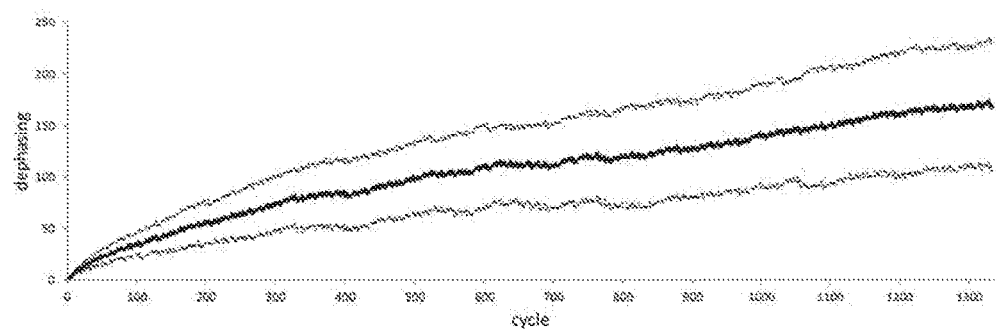
FIG. 5A / FIG. 5B
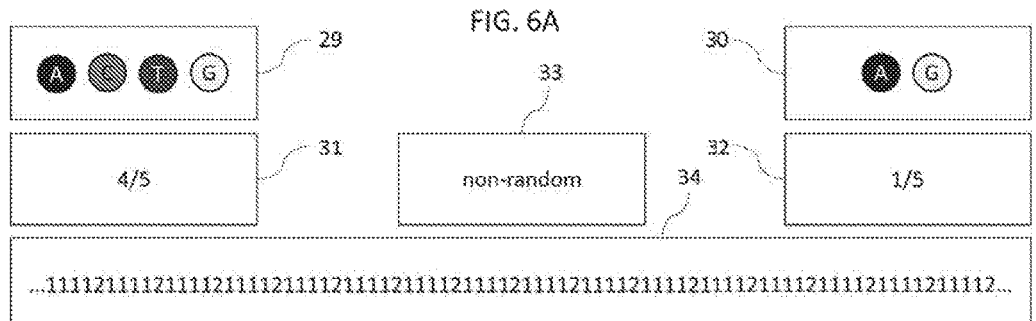
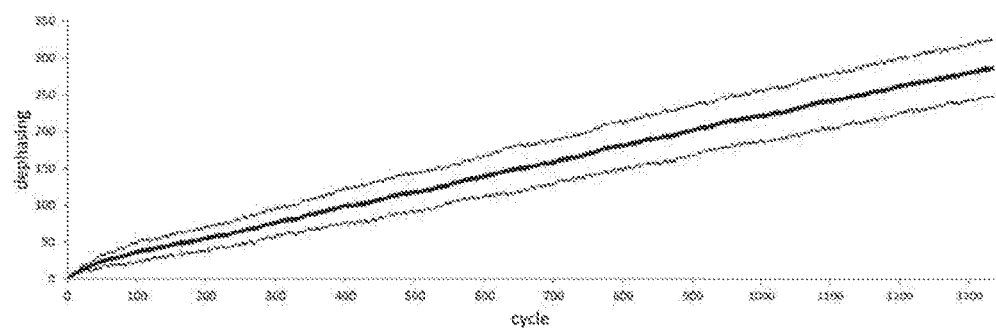
FIG. 6A / FIG. 6B

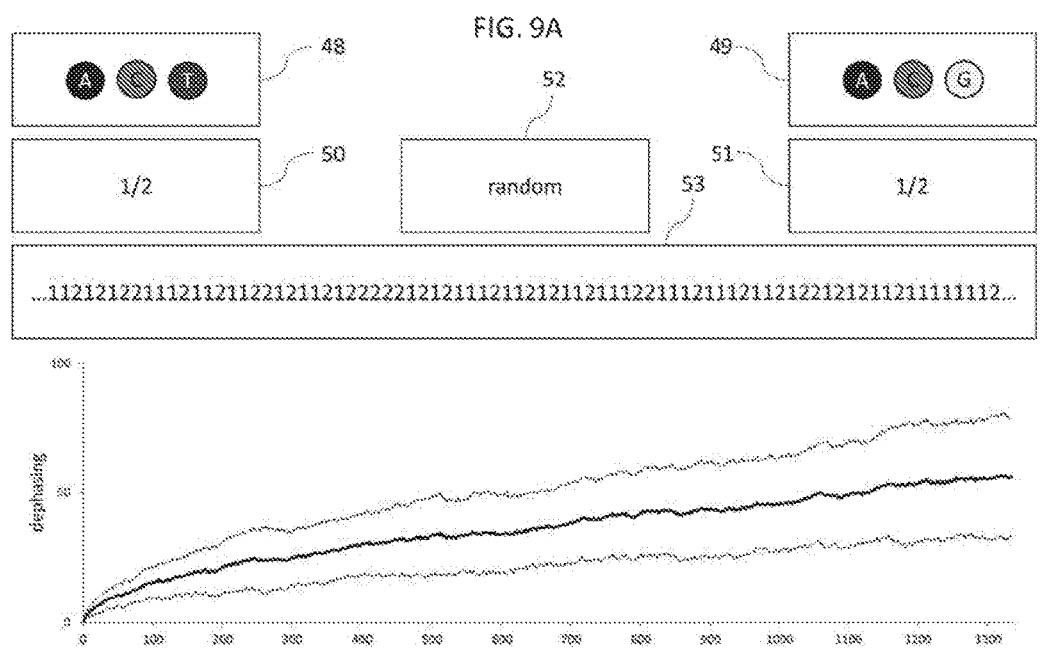
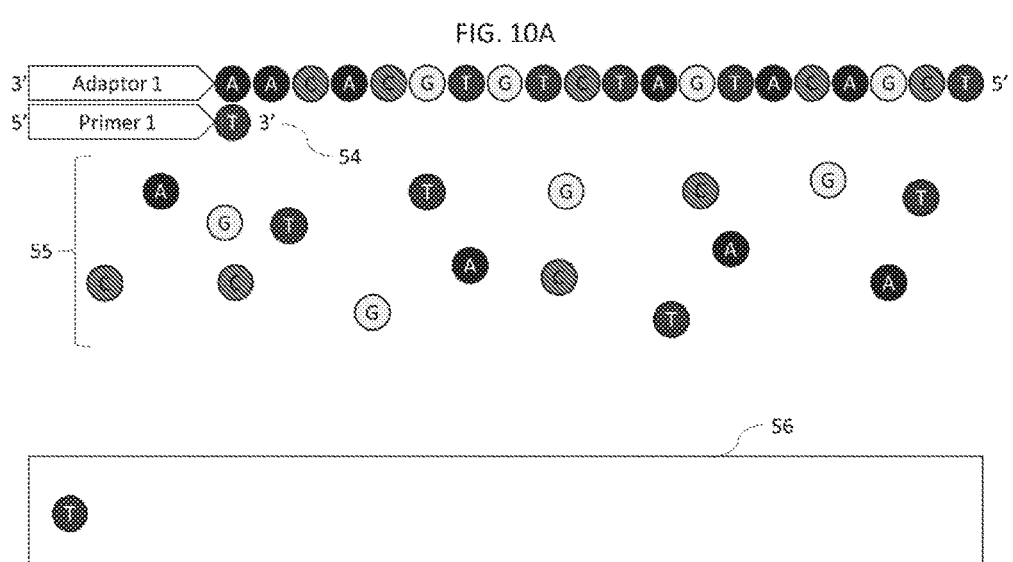

FIG. 10F
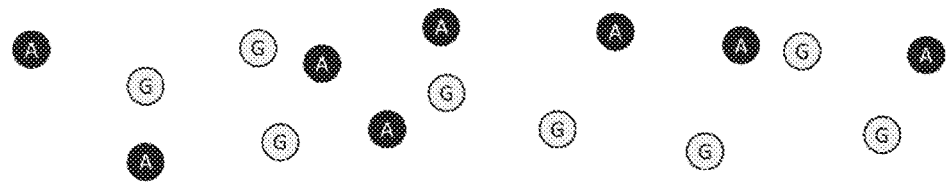
FIG. 10G
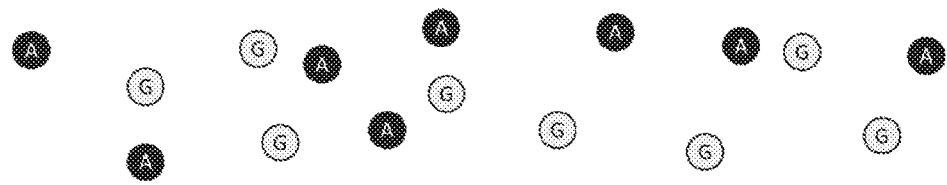

FIG. 11C
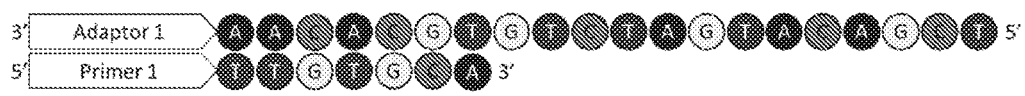
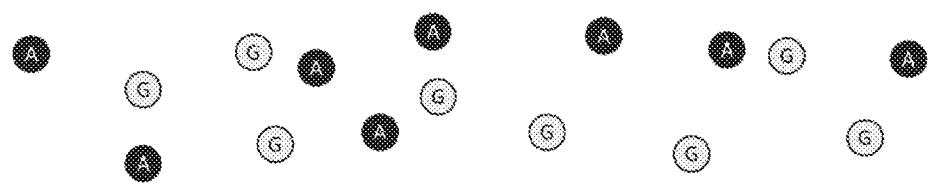
FIG. 12A
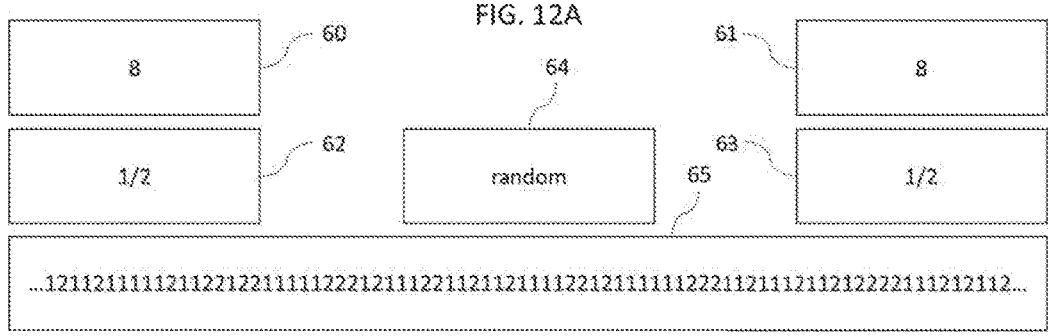
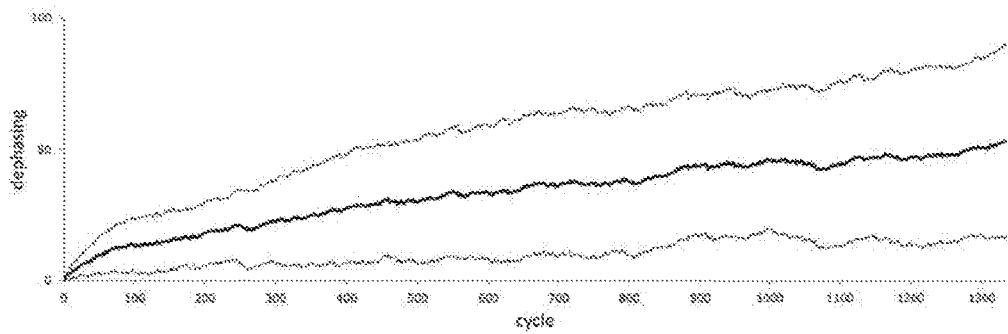
FIG. 12B

METHOD FOR REDUCING DEPHASING DURING CLUSTER DNA SEQUENCING

RELATED APPLICATION

This application claims the benefit of U.S. Provisional Application Ser. No. 62/189,801 filed on 8 Jul. 2015, which is incorporated by reference herein.

FIELD OF THE INVENTION

The present invention generally relates to the field of cluster DNA sequencing. More particularly, the present invention comprises a method to return out-of-phase amplicons back into phase. Specifically, this method comprises an alternative method for flowing nucleotides or oligonucleotides in order to give out-of-phase amplicons the opportunity to get back in-phase and allow longer DNA sequences to be obtained.

BACKGROUND OF THE INVENTION

Clusters containing multiple copies of the same sequence are used to enhance the signal intensity from the incorporation of nucleotides when sequencing by synthesis or the incorporation of oligonucleotides when using 2 base encoded sequencing, also called SOLiD (Sequencing by Oligonucleotide Ligation and Detection). This relies on the sequences being in-phase and the same nucleotide or oligonucleotide being incorporated onto each growing amplicon at the same time in the cluster. However, individual amplicons can become out-of-phase (dephasing) due to nucleotides or oligonucleotides being under- or over-incorporated. As sequencing progresses these accumulate and this reduces the accuracy of base calling.

BRIEF SUMMARY OF THE INVENTION

The invention present is a method to resynchronize nucleotide or oligonucleotide incorporation in DNA clusters for sequencing by synthesis or 2 base encoded sequencing. By excluding one or more nucleotide species or oligonucleotide species from some or all extension cycles, out-of-phase amplicons (FIG. 1) can become in-phase (FIG. 11A-11C). Using this method, sequencing accuracy can be maintained with increasing read length.

Using a DNA sequencing method comprising a single nucleotide solution comprising all four nucleotide species (dATP dTTP dCTP dGTP) such as those used in various Illumina (Solexa) sequencing platforms, two out-of-phase amplicons will each incorporate a single nucleotide species each cycle and remain out-of-phase. However, using a DNA sequencing method comprising two nucleotide solutions, one nucleotide solution comprising four nucleotide species (dATP dTTP dCTP dGTP) and one nucleotide solution comprising two nucleotide species (dATP dGTP), when the nucleotide solution comprising two nucleotide species is flowed, only amplicons which require one of the nucleotide species flowed (dATP or dGTP) will extend, while amplicons which require one of the nucleotide species not flowed (dTTP or dCTP) will not extend. If the nucleotide solution to be flowed is randomly selected each cycle, the number of nucleotides by which two out-of-phase amplicons differ will increase and decrease randomly until this number becomes fixed at zero and the amplicons have become in-phase. Similarly, when using 2 base encoded sequencing (SOLiD), a method comprising at least one oligonucleotide solution comprising less than the complete set of sixteen oligonucleotide species flowed in an order of flow which is not a continuous repeat of a single flow of each oligonucleotide solution can be used to enable dephased amplicons to become in-phase.

Any method where at least two different nucleotide solutions or oligonucleotide solutions are flowed in an order of flow which is not a repeat of an ordering of each nucleotide solution or oligonucleotide solution can be used to reduce dephasing by returning amplicons which become out-of-phase back in-phase. Different nucleotide solution or oligonucleotide solution and flow ordering combinations can have different effects on the frequency with which dephased amplicons return back in-phase. Specifically, the greater the percentage of cycles in which an out-of-phase amplicon incorporates a nucleotide or oligonucleotide and the in-phase amplicons do not, or the in-phase amplicons incorporate a nucleotide or oligonucleotide and an out-of-phase amplicon does not, the better the method for decreasing dephasing.

BRIEF DESCRIPTION OF THE DRAWINGS

The accompanying drawings, which are incorporated in and constitute a part of this specification, illustrate one or more exemplary embodiments and serve to explain the principles of various exemplary embodiments. The drawings are merely exemplary and explanatory and should in no way be construed as limiting or restrictive.

FIG. 1 discloses SEQ ID NO: 1, SEQ ID NO: 2, SEQ ID NO: 3 and SEQ ID NO: 4.

FIG. 5A illustrates another exemplary set of nucleotide solutions and an exemplary order of flow and FIG. 5B illustrates the average of 100 sequencing simulations using those conditions.

FIG. 6A illustrates another exemplary set of nucleotide solutions and an exemplary order of flow and FIG. 6B illustrates the average of 100 sequencing simulations using those conditions.

FIG. 9A illustrates another exemplary set of nucleotide solutions and an exemplary order of flow and FIG. 9B illustrates the average of 100 sequencing simulations using those conditions.

FIG. 10A-10Q disclose SEQ ID NO: 1, FIG. 10L discloses SEQ ID NO: 5, FIG. 10M discloses SEQ ID NO: 6, FIG. 10N discloses SEQ ID NO: 3, FIG. 10O discloses SEQ ID NO: 3, FIG. 10P discloses SEQ ID NO: 2 and FIG. 10Q discloses SEQ ID NO: 4.

FIG. 11A-11C illustrate schematically an example of how an embodiment of the method described herein, can resynchronise out-of-phase amplicons. FIG. 11A-11C disclose SEQ ID NO: 1.

FIG. 12A illustrates an exemplary set of oligonucleotide solutions and an exemplary order of flow and FIG. 12B illustrates the average of 100 sequencing simulations using those conditions.

DETAILED DESCRIPTION OF THE INVENTION

Figure 1:
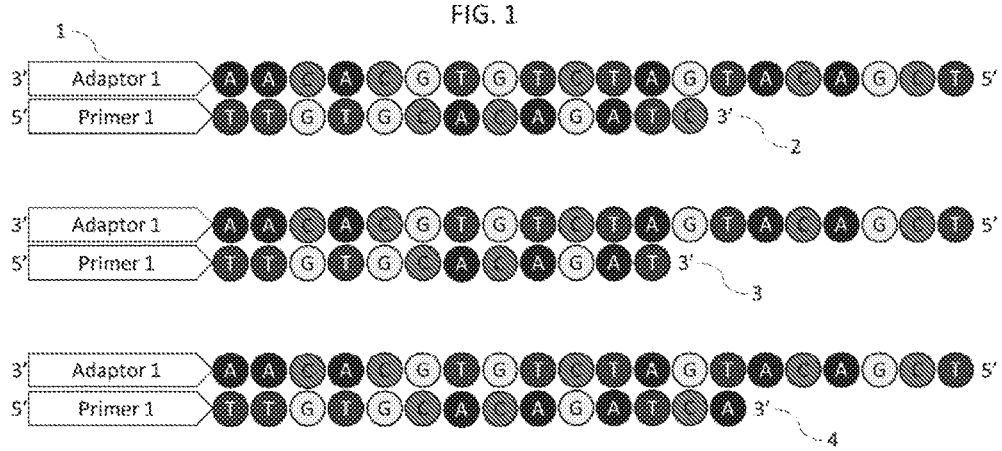
FIG. 1 illustrates exemplary amplicons showing leading strand and lagging strand dephasing.

The following description and the various embodiments described herein are merely exemplary and explanatory and should in no way be construed as limiting or restrictive. The possible embodiments of the teachings of the invention present are too numerous to describe herein and other embodiments are obvious from the claims, drawings and description.

Unless expressly stated herein, terms relating to molecular biology, biochemistry, genetics, nucleic acid chemistry and statistics follow those standards of papers and textbooks from related fields.

In various embodiments, a single nucleotide solution can contain all four nucleotide species (dATP dTTP dCTP dGTP), three nucleotide species (dATP dTTP dCTP or dATP dTTP dGTP or dATP dCTP dGTP or dTTP dCTP dGTP), two nucleotide species (dATP dTTP or dATP dCTP or dATP dGTP or dTTP dCTP or dTTP dGTP or dCTP dGTP) or one nucleotide species (dATP or dTTP or dCTP or dGTP). Although the preferred embodiment uses only two different nucleotide solutions, three, four, five, six, seven, eight, nine, ten, eleven, twelve, thirteen, fourteen or fifteen different nucleotide solutions could also be used without departing from the scope of these teachings.

In various embodiments, the method comprises two different nucleotide solutions, one nucleotide solution comprising all four nucleotide species (dATP dTTP dCTP dGTP) and one nucleotide solution comprising three nucleotide species (dATP dTTP dCTP or dATP dTTP dGTP or dATP dCTP dGTP or dTTP dCTP dGTP).

In various embodiments, the method comprises two different nucleotide solutions, one nucleotide solution comprising all four nucleotide species (dATP dTTP dCTP dGTP) and one nucleotide solution comprising two nucleotide species (dATP dTTP or dATP dCTP or dATP dGTP or dTTP dCTP or dTTP dGTP or dCTP dGTP).

In various embodiments, the method comprises two different nucleotide solutions, one nucleotide solution comprising all four nucleotide species (dATP dTTP dCTP dGTP) and one nucleotide solution comprising one nucleotide species (dATP or dTTP or dCTP or dGTP).

In various embodiments, the method comprises two different nucleotide solutions each comprising three nucleotide species (dATP dTTP dCTP or dATP dTTP dGTP or dATP dCTP dGTP or dTTP dCTP dGTP).

In various embodiments, the method comprises two different nucleotide solutions, one nucleotide solution comprising three nucleotide species (dATP dTTP dCTP or dATP dTTP dGTP or dATP dCTP dGTP or dTTP dCTP dGTP) and one nucleotide solution comprising two nucleotide species (dATP dTTP or dATP dCTP or dATP dGTP or dTTP dCTP or dTTP dGTP or dCTP dGTP) and between the two nucleotide solutions, all four nucleotide species are comprised therein.

In various embodiments, the method comprises two different nucleotide solutions, one nucleotide solution comprising three nucleotide species (dATP dTTP dCTP or dATP dTTP dGTP or dATP dCTP dGTP or dTTP dCTP dGTP) and one nucleotide solution comprising one nucleotide species (dATP or dTTP or dCTP or dGTP) and between the two nucleotide solutions, all four nucleotide species are comprised therein.

In various embodiments, the method comprises two different nucleotide solutions each comprising two nucleotide species (dATP dTTP or dATP dCTP or dATP dGTP or dTTP dCTP or dTTP dGTP or dCTP dGTP) and between the two nucleotide solutions, all four nucleotide species are comprised therein.

In various embodiments, the method comprises three different nucleotide solutions, one nucleotide solution comprising all four nucleotide species (dATP dTTP dCTP dGTP) and two nucleotide solutions each comprising three nucleotide species (dATP dTTP dCTP or dATP dTTP dGTP or dATP dCTP dGTP or dTTP dCTP dGTP).

In various embodiments, the method comprises three different nucleotide solutions, one nucleotide solution comprising all four nucleotide species (dATP dTTP dCTP dGTP), one nucleotide solution comprising three nucleotide species (dATP dTTP dCTP or dATP dTTP dGTP or dATP dCTP dGTP or dTTP dCTP dGTP) and one nucleotide solution comprising two nucleotide species (dATP dTTP or dATP dCTP or dATP dGTP or dTTP dCTP or dTTP dGTP or dCTP dGTP).

In various embodiments, the method comprises three different nucleotide solutions, one nucleotide solution comprising all four nucleotide species (dATP dTTP dCTP dGTP), one nucleotide solution comprising three nucleotide species (dATP dTTP dCTP or dATP dTTP dGTP or dATP dCTP dGTP or dTTP dCTP dGTP) and one nucleotide solution comprising one nucleotide species (dATP or dTTP or dCTP or dGTP).

In various embodiments, the method comprises three different nucleotide solutions, one nucleotide solution comprising all four nucleotide species (dATP dTTP dCTP dGTP) and two nucleotide solutions each comprising two nucleotide species (dATP dTTP or dATP dCTP or dATP dGTP or dTTP dCTP or dTTP dGTP or dCTP dGTP).

In various embodiments, the method comprises three different nucleotide solutions, one nucleotide solution comprising all four nucleotide species (dATP dTTP dCTP dGTP), one nucleotide solution comprising two nucleotide species (dATP dTTP or dATP dCTP or dATP dGTP or dTTP dCTP or dTTP dGTP or dCTP dGTP) and one nucleotide solution comprising one nucleotide species (dATP or dTTP or dCTP or dGTP).

In various embodiments, the method comprises three different nucleotide solutions, one nucleotide solution comprising all four nucleotide species (dATP dTTP dCTP dGTP) and two nucleotide solutions each comprising one nucleotide species (dATP or dTTP or dCTP or dGTP).

In various embodiments, the method comprises three different nucleotide solutions each comprising three nucleotide species (dATP dTTP dCTP or dATP dTTP dGTP or dATP dCTP dGTP or dTTP dCTP dGTP).

In various embodiments, the method comprises three different nucleotide solutions, two nucleotide solutions each comprising three nucleotide species (dATP dTTP dCTP or dATP dTTP dGTP or dATP dCTP dGTP or dTTP dCTP dGTP) and one nucleotide solution comprising two nucleotide species (dATP dTTP or dATP dCTP or dATP dGTP or dTTP dCTP or dTTP dGTP or dCTP dGTP).

In various embodiments, the method comprises three different nucleotide solutions, two nucleotide solutions each comprising three nucleotide species (dATP dTTP dCTP or dATP dTTP dGTP or dATP dCTP dGTP or dTTP dCTP dGTP) and one nucleotide solution comprising one nucleotide species (dATP or dTTP or dCTP or dGTP).

In various embodiments, the method comprises three different nucleotide solutions, one nucleotide solution comprising three nucleotide species (dATP dTTP dCTP or dATP dTTP dGTP or dATP dCTP dGTP or dTTP dCTP dGTP) and two nucleotide solutions each comprising two nucleotide species (dATP dTTP or dATP dCTP or dATP dGTP or dTTP dCTP or dTTP dGTP or dCTP dGTP) and between the three nucleotide solutions, all four nucleotide species are comprised therein.

In various embodiments, the method comprises three different nucleotide solutions, one nucleotide solution comprising three nucleotide species (dATP dTTP dCTP or dATP dTTP dGTP or dATP dCTP dGTP or dTTP dCTP dGTP), one nucleotide solution comprising two nucleotide species (dATP dTTP or dATP dCTP or dATP dGTP or dTTP dCTP or dTTP dGTP or dCTP dGTP), and one nucleotide solution comprising one nucleotide species (dATP or dTTP or dCTP or dGTP) and between the three nucleotide solutions, all four nucleotide species are comprised therein.

In various embodiments, the method comprises three different nucleotide solutions, one nucleotide solution comprising three nucleotide species (dATP dTTP dCTP or dATP dTTP dGTP or dATP dCTP dGTP or dTTP dCTP dGTP) and two nucleotide solutions each comprising one nucleotide species (dATP or dTTP or dCTP or dGTP) and between the three nucleotide solutions, all four nucleotide species are comprised therein.

In various embodiments, the method comprises three different nucleotide solutions each comprising two nucleotide species (dATP dTTP or dATP dCTP or dATP dGTP or dTTP dCTP or dTTP dGTP or dCTP dGTP) and between the three nucleotide solutions, all four nucleotide species are comprised therein.

In various embodiments, the method comprises three different nucleotide solutions, two nucleotide solutions each comprising two nucleotide species (dATP dTTP or dATP dCTP or dATP dGTP or dTTP dCTP or dTTP dGTP or dCTP dGTP) and one nucleotide solution comprising one nucleotide species (dATP or dTTP or dCTP or dGTP) and between the three nucleotide solutions, all four nucleotide species are comprised therein.

In various embodiments, the method comprises three different nucleotide solutions, one nucleotide solution comprising two nucleotide species (dATP dTTP or dATP dCTP or dATP dGTP or dTTP dCTP or dTTP dGTP or dCTP dGTP) and two nucleotide solutions each comprising one nucleotide species (dATP or dTTP or dCTP or dGTP) and between the three nucleotide solutions, all four nucleotide species are comprised therein.

In various embodiments, the method comprises four different nucleotide solutions, one nucleotide solution comprising all four nucleotide species (dATP dTTP dCTP dGTP) and three nucleotide solutions each comprising three nucleotide species (dATP dTTP dCTP or dATP dTTP dGTP or dATP dCTP dGTP or dTTP dCTP dGTP).

In various embodiments, the method comprises four different nucleotide solutions, one nucleotide solution comprising all four nucleotide species (dATP dTTP dCTP dGTP), two nucleotide solutions each comprising three nucleotide species (dATP dTTP dCTP or dATP dTTP dGTP or dATP dCTP dGTP or dTTP dCTP dGTP) and one nucleotide solution comprising two nucleotide species (dATP dTTP or dATP dCTP or dATP dGTP or dTTP dCTP or dTTP dGTP or dCTP dGTP).

In various embodiments, the method comprises four different nucleotide solutions, one nucleotide solution comprising all four nucleotide species (dATP dTTP dCTP dGTP), two nucleotide solutions each comprising three nucleotide species (dATP dTTP dCTP or dATP dTTP dGTP or dATP dCTP dGTP or dTTP dCTP dGTP) and one nucleotide solution comprising one nucleotide species (dATP or dTTP or dCTP or dGTP).

In various embodiments, the method comprises four different nucleotide solutions, one nucleotide solution comprising all four nucleotide species (dATP dTTP dCTP dGTP), one nucleotide solution comprising three nucleotide species (dATP dTTP dCTP or dATP dTTP dGTP or dATP dCTP dGTP or dTTP dCTP dGTP) and two nucleotide solutions each comprising two nucleotide species (dATP dTTP or dATP dCTP or dATP dGTP or dTTP dCTP or dTTP dGTP or dCTP dGTP).

In various embodiments, the method comprises four different nucleotide solutions, one nucleotide solution comprising all four nucleotide species (dATP dTTP dCTP dGTP), one nucleotide solution comprising three nucleotide species (dATP dTTP dCTP or dATP dTTP dGTP or dATP dCTP dGTP or dTTP dCTP dGTP), one nucleotide solution comprising two nucleotide species (dATP dTTP or dATP dCTP or dATP dGTP or dTTP dCTP or dTTP dGTP or dCTP dGTP) and one nucleotide solution comprising one nucleotide species (dATP or dTTP or dCTP or dGTP).

In various embodiments, the method comprises four different nucleotide solutions, one nucleotide solution comprising all four nucleotide species (dATP dTTP dCTP dGTP), one nucleotide solution comprising three nucleotide species (dATP dTTP dCTP or dATP dTTP dGTP or dATP dCTP dGTP or dTTP dCTP dGTP) and two nucleotide solutions each comprising one nucleotide species (dATP or dTTP or dCTP or dGTP).

In various embodiments, the method comprises four different nucleotide solutions, one nucleotide solution comprising all four nucleotide species (dATP dTTP dCTP dGTP) and three nucleotide solutions each comprising two nucleotide species (dATP dTTP or dATP dCTP or dATP dGTP or dTTP dCTP or dTTP dGTP or dCTP dGTP).

In various embodiments, the method comprises four different nucleotide solutions, one nucleotide solution comprising all four nucleotide species (dATP dTTP dCTP dGTP), two nucleotide solutions each comprising two nucleotide species (dATP dTTP or dATP dCTP or dATP dGTP or dTTP dCTP or dTTP dGTP or dCTP dGTP) and one nucleotide solution comprising one nucleotide species (dATP or dTTP or dCTP or dGTP).

In various embodiments, the method comprises four different nucleotide solutions, one nucleotide solution comprising all four nucleotide species (dATP dTTP dCTP dGTP), one nucleotide solution comprising two nucleotide species (dATP dTTP or dATP dCTP or dATP dGTP or dTTP dCTP or dTTP dGTP or dCTP dGTP) and two nucleotide solutions each comprising one nucleotide species (dATP or dTTP or dCTP or dGTP).

In various embodiments, the method comprises four different nucleotide solutions, one nucleotide solution comprising all four nucleotide species (dATP dTTP dCTP dGTP) and three nucleotide solutions each comprising one nucleotide species (dATP or dTTP or dCTP or dGTP).

In various embodiments, the method comprises four different nucleotide solutions each comprising three nucleotide species (dATP dTTP dCTP or dATP dTTP dGTP or dATP dCTP dGTP or dTTP dCTP dGTP).

In various embodiments, the method comprises four different nucleotide solutions, three nucleotide solutions each comprising three nucleotide species (dATP dTTP dCTP or dATP dTTP dGTP or dATP dCTP dGTP or dTTP dCTP dGTP) and one nucleotide solution comprising two nucleotide species (dATP dTTP or dATP dCTP or dATP dGTP or dTTP dCTP or dTTP dGTP or dCTP dGTP).

In various embodiments, the method comprises four different nucleotide solutions, three nucleotide solutions each comprising three nucleotide species (dATP dTTP dCTP or dATP dTTP dGTP or dATP dCTP dGTP or dTTP dCTP dGTP) and one nucleotide solution comprising one nucleotide species (dATP or dTTP or dCTP or dGTP).

In various embodiments, the method comprises four different nucleotide solutions, two nucleotide solutions each comprising three nucleotide species (dATP dTTP dCTP or dATP dTTP dGTP or dATP dCTP dGTP or dTTP dCTP dGTP) and two nucleotide solutions each comprising two nucleotide species (dATP dTTP or dATP dCTP or dATP dGTP or dTTP dCTP or dTTP dGTP or dCTP dGTP).

In various embodiments, the method comprises four different nucleotide solutions, two nucleotide solutions each comprising three nucleotide species (dATP dTTP dCTP or dATP dTTP dGTP or dATP dCTP dGTP or dTTP dCTP dGTP), one nucleotide solution comprising two nucleotide species (dATP dTTP or dATP dCTP or dATP dGTP or dTTP dCTP or dTTP dGTP or dCTP dGTP) and one nucleotide solution comprising one nucleotide species (dATP or dTTP or dCTP or dGTP).

In various embodiments, the method comprises four different nucleotide solutions, two nucleotide solutions each comprising three nucleotide species (dATP dTTP dCTP or dATP dTTP dGTP or dATP dCTP dGTP or dTTP dCTP dGTP) and two nucleotide solutions each comprising one nucleotide species (dATP or dTTP or dCTP or dGTP).

In various embodiments, the method comprises four different nucleotide solutions, one nucleotide solution comprising three nucleotide species (dATP dTTP dCTP or dATP dTTP dGTP or dATP dCTP dGTP or dTTP dCTP dGTP) and three nucleotide solutions each comprising two nucleotide species (dATP dTTP or dATP dCTP or dATP dGTP or dTTP dCTP or dTTP dGTP or dCTP dGTP) and between the four nucleotide solutions, all four nucleotide species are comprised therein.

In various embodiments, the method comprises four different nucleotide solutions, one nucleotide solution comprising three nucleotide species (dATP dTTP dCTP or dATP dTTP dGTP or dATP dCTP dGTP or dTTP dCTP dGTP), two nucleotide solutions each comprising two nucleotide species (dATP dTTP or dATP dCTP or dATP dGTP or dTTP dCTP or dTTP dGTP or dCTP dGTP) and one nucleotide solution comprising one nucleotide species (dATP or dTTP or dCTP or dGTP) and between the four nucleotide solutions, all four nucleotide species are comprised therein.

In various embodiments, the method comprises four different nucleotide solutions, one nucleotide solution comprising three nucleotide species (dATP dTTP dCTP or dATP dTTP dGTP or dATP dCTP dGTP or dTTP dCTP dGTP), one nucleotide solution comprising two nucleotide species (dATP dTTP or dATP dCTP or dATP dGTP or dTTP dCTP or dTTP dGTP or dCTP dGTP) and two nucleotide solutions each comprising one nucleotide species (dATP or dTTP or dCTP or dGTP) and between the four nucleotide solutions, all four nucleotide species are comprised therein.

In various embodiments, the method comprises four different nucleotide solutions, one nucleotide solution comprising three nucleotide species (dATP dTTP dCTP or dATP dTTP dGTP or dATP dCTP dGTP or dTTP dCTP dGTP) and three nucleotide solutions each comprising one nucleotide species (dATP or dTTP or dCTP or dGTP) and between the four nucleotide solutions, all four nucleotide species are comprised therein.

In various embodiments, the method comprises four different nucleotide solutions each comprising two nucleotide species (dATP dTTP or dATP dCTP or dATP dGTP or dTTP dCTP or dTTP dGTP or dCTP dGTP).

In various embodiments, the method comprises four different nucleotide solutions, three nucleotide solutions each comprising two nucleotide species (dATP dTTP or dATP dCTP or dATP dGTP or dTTP dCTP or dTTP dGTP or dCTP dGTP) and one nucleotide solution comprising one nucleotide species (dATP or dTTP or dCTP or dGTP) and between the four nucleotide solutions, all four nucleotide species are comprised therein.

In various embodiments, the method comprises four different nucleotide solutions, two nucleotide solutions each comprising two nucleotide species (dATP dTTP or dATP dCTP or dATP dGTP or dTTP dCTP or dTTP dGTP or dCTP dGTP) and two nucleotide solutions each comprising one nucleotide species (dATP or dTTP or dCTP or dGTP) and between the four nucleotide solutions, all four nucleotide species are comprised therein.

In various embodiments, the method comprises four different nucleotide solutions, one nucleotide solution comprising two nucleotide species (dATP dTTP or dATP dCTP or dATP dGTP or dTTP dCTP or dTTP dGTP or dCTP dGTP) and three nucleotide solutions each comprising one nucleotide species (dATP or dTTP or dCTP or dGTP) and between the four nucleotide solutions, all four nucleotide species are comprised therein.

In various embodiments, the method comprises four different nucleotide solutions each comprising one nucleotide species (dATP or dTTP or dCTP or dGTP).

In various embodiments, the method comprises more than four different nucleotide solutions each comprising one to four nucleotide species (dATP dTTP dCTP dGTP or dATP dTTP dCTP or dATP dTTP dGTP or dATP dCTP dGTP or dTTP dCTP dGTP or dATP dTTP or dATP dCTP or dATP dGTP or dTTP dCTP or dTTP dGTP or dCTP dGTP or dATP or dTTP or dCTP or dGTP) and between the nucleotide solutions, all four nucleotide species are comprised therein.

In various embodiments, the order of flow is at least in part a repeat of an ordering of the nucleotide solutions with a smallest repeating unit which is greater than a single flow of each of the nucleotide solutions.

In various embodiments, the smallest repeating unit can be comprised of equal parts of each of the nucleotide solutions. For example, a method which comprises four different nucleotide solutions could have a smallest repeating unit 1, 2, 3, 4, 2, 3, 4, 1, 3, 4, 1, 2, 4, 1, 2, 3. In another example, a method which comprises four different nucleotide solutions and a smallest repeating unit of 1, 2, 3, 4 (comprised of a single flow of each nucleotide solution) is not included in the scope of these teachings.

In various embodiments, the smallest repeating unit can be comprised of unequal parts of each or some of the nucleotide solutions. For example, a method which comprises two different nucleotide solutions could have a smallest repeating unit 1, 1, 1, 1, 2, 1, 1, 2, 1, 1, 1, 1, 1, 1, 2, 1, 1, 1, 2, 1, 1, 1, 1, 1, 2 (FIGS. 5A and 5B). In this example, the nucleotide solution '2' is flowed on average one in five cycles, but any ratio could be used without departing from the scope of these teachings. The various possible smallest repeating units are too numerous to mention here, so it is to be understood that any smallest repeating unit, which is not comprised of a single flow of each nucleotide solution, is included in the scope of these teachings.

In various embodiments, out-of-phase amplicons which become out-of-phase by the number of cycles of the smallest repeating unit would be exposed to flows of the same nucleotide solution at the same position on the DNA template and remain out-of-phase by the number of cycles of the smallest repeating unit. The likelihood of amplicons becoming one smallest repeating unit out-of-phase becomes greater the shorter the smallest repeating unit. For example, for a method comprising two nucleotide solutions, a smallest repeating unit of 1, 1, 1, 1, 2 (FIGS. 6A and 6B) would trap more out-of-phase amplicons one repeating unit out-of-phase than a smallest repeating unit of 1, 1, 1, 1, 1, 2, 1, 1, 1, 2. Although a long smallest repeating unit is preferred, it is understood that any smallest repeating unit larger than a single flow of each nucleotide solution is within the scope of these teachings.

In various embodiments, the order of flow is at least in part a random ordering of the nucleotide solutions where the nucleotide solution to be flowed is selected randomly by any means of random selection. The random selection could comprise equal probability of selection for each nucleotide solution. Alternatively, the random selection could comprise unequal probability of selection between at least two nucleotide solutions.

In various embodiments, one or more nucleotide solutions can be flowed more frequently than one or more other nucleotide solutions. For example, a nucleotide solution could be flowed on average one cycle in two cycles or one cycle in three cycles (FIGS. 2A and 2B) or one cycle in four cycles (FIGS. 3A and 3B) or one cycle in five cycles (FIGS. 4A and 4B) or one cycle in six cycles or one cycle in any number of cycles greater than one and less than the length of the sequencing run. There is an infinite number of possible frequencies which could be used (for example, a nucleotide solution could be flowed on average one cycle in 5.4385623 cycles) so it is to be understood that any frequency can be used without departing from the scope of these teachings.

In various embodiments, the probability of random selection of a flow of one nucleotide solution following random selection of a flow of a different nucleotide solution is greater than the probability of random selection of a flow of one nucleotide solution following random selection of a flow of the same nucleotide solution.

Figure 8A:
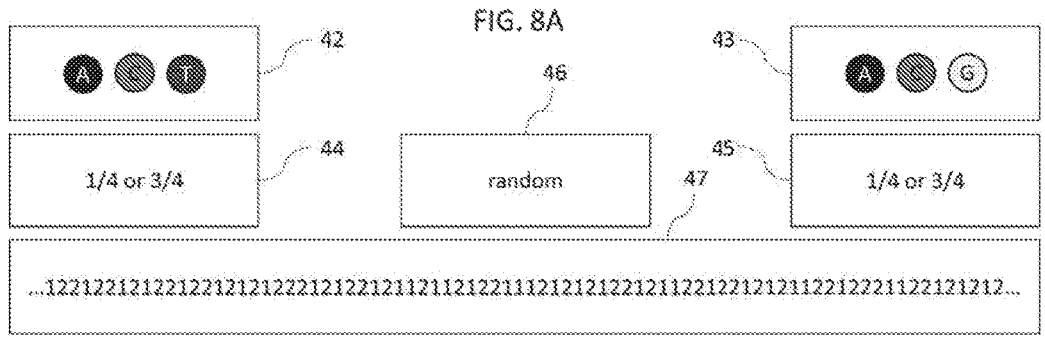
FIG. 8A illustrates another exemplary set of nucleotide solutions and an exemplary order of flow and FIG. 8B illustrates the average of 100 sequencing simulations using those conditions.
Figure 8B:
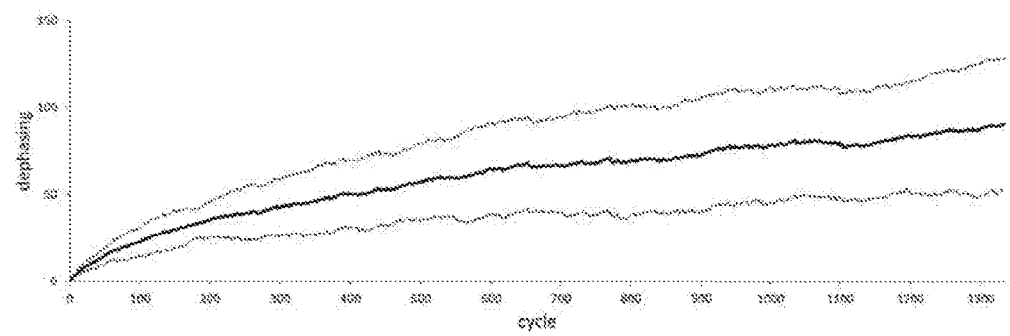

In various embodiments, a nucleotide solution that is selected to be flowed in one cycle could have a smaller probability of being selected to be flowed in the next cycle. For example, for a method which comprises two nucleotide solutions, the nucleotide solution which was selected in the previous cycle can have a one in four probability of being selected for the next cycle. In which case the nucleotide solution which was not selected to be flowed in the previous cycle would have a three in four probability of being selected to be flowed in the next cycle (FIGS. 8A and 8B).

In various embodiments, at least one nucleotide solution cannot be flowed two cycles in a row. For example, a method comprising two nucleotide solutions, one comprising all four nucleotide species and one comprising two nucleotide species, one flow of the two-nucleotide species solution is always followed by at least one flow of the four-nucleotide species solution.

In various embodiments, more than one nucleotide solution can be flowed in the same cycle. For example, in a method comprising two nucleotide solutions, each comprising two nucleotide species and together comprising all four nucleotide species, both nucleotide solutions could be flowed in a single cycle. In such a cycle, all four nucleotide species would be flowed. In this way, two different nucleotide solutions could make three different nucleotide solutions without departing from the scope of these teachings.

In various embodiments, the frequencies of nucleotide solution flow can change as sequencing progresses. Numerous frequencies of selection can be applied for a single nucleotide solution during a single sequencing run without departing from the scope of these teachings.

In various embodiments, the method comprises two different oligonucleotide solutions each comprising eight oligonucleotide species and between the two oligonucleotide solutions, all sixteen oligonucleotide species are comprised therein.

In various embodiments, the method comprises two different oligonucleotide solutions, one oligonucleotide solution comprising sixteen oligonucleotide species (with 3' nucleotides AA, AT, AC, AG, TA, TT, TC, TG, CA, CT, CC, CG, GA, GT, GC and GG) and one oligonucleotide solution comprising eight oligonucleotide species and between the two oligonucleotide solutions, all sixteen oligonucleotide species are comprised therein.

In various embodiments, the method comprises more than one different oligonucleotide solutions each comprising one to sixteen oligonucleotide species (with 3' nucleotides AA, AT, AC, AG, TA, TT, TC, TG, CA, CT, CC, CG, GA, GT, GC and GG) and between the oligonucleotide solutions, all sixteen oligonucleotide species are comprised therein.

In various embodiments, the method comprises two different oligonucleotide solutions, one comprising sixteen oligonucleotide species (with 3' nucleotides AA, AT, AC, AG, TA, TT, TC, TG, CA, CT, CC, CG, GA, GT, GC and GG) and one comprising eight oligonucleotide species.

In various embodiments, the order of flow is at least in part a repeat of an ordering of the oligonucleotide solutions with a smallest repeating unit which is greater than a single flow of each of the oligonucleotide solutions.

In various embodiments, the smallest repeating unit can be comprised of equal parts of each of the oligonucleotide solutions. For example, a method which comprises four different oligonucleotide solutions could have a smallest repeating unit 1, 2, 3, 4, 2, 3, 4, 1, 3, 4, 1, 2, 4, 1, 2, 3. In another example, a method which comprises four different oligonucleotide solutions and a smallest repeating unit of 1, 2, 3, 4 (comprised of a single flow of each oligonucleotide solution) is not included in the scope of these teachings.

In various embodiments, the smallest repeating unit can be comprised of unequal parts of each or some of the oligonucleotide solutions. For example, a method which comprises two different oligonucleotide solutions could have a smallest repeating unit 1, 1, 1, 1, 2, 1, 1, 2, 1, 1, 1, 1, 1, 1, 2, 1, 1, 1, 2, 1, 1, 1, 1, 1, 2 (FIGS. 5A and 5B). In this example, the oligonucleotide solution '2' is flowed on average one in five cycles, but any ratio could be used without departing from the scope of these teachings. The various possible smallest repeating units are too numerous to mention here, so it is to be understood that any smallest repeating unit, which is not comprised of a single flow of each oligonucleotide solution, is included in the scope of these teachings.

In various embodiments, out-of-phase amplicons which become out-of-phase by the number of cycles of the smallest repeating unit would be exposed to flows of the same oligonucleotide solution at the same position on the DNA template and remain out-of-phase by the number of cycles of the smallest repeating unit. The likelihood of amplicons becoming one smallest repeating unit out-of-phase becomes greater the shorter the smallest repeating unit. For example, for a method comprising two oligonucleotide solutions, a smallest repeating unit of 1, 1, 1, 1, 2 would trap more out-of-phase amplicons one repeating unit out-of-phase than a smallest repeating unit of 1, 1, 1, 1, 1, 2, 1, 1, 1, 2. Although a long smallest repeating unit is preferred, it is understood that any smallest repeating unit larger than a single flow of each oligonucleotide solution is within the scope of these teachings.

In various embodiments, the order of flow is at least in part a random ordering of the oligonucleotide solutions where the oligonucleotide solution to be flowed is selected randomly by any means of random selection. The random selection could comprise equal probability of selection for each oligonucleotide solution. Alternatively, the random selection could comprise unequal probability of selection between at least two oligonucleotide solutions.

In various embodiments, one or more oligonucleotide solutions can be flowed more frequently than one or more other oligonucleotide solutions. For example, an oligonucleotide solution could be flowed on average one cycle in two cycles (FIGS. 12A and 12B and FIGS. 13A and 13B) or one cycle in three cycles or one cycle in four cycles or one cycle in five cycles or one cycle in six cycles or one cycle in any number of cycles greater than one and less than the length of the sequencing run. There is an infinite number of possible frequencies which could be used (for example, an oligonucleotide solution could be flowed on average one cycle in 5.4385623 cycles) so it is to be understood that any frequency can be used without departing from the scope of these teachings.

In various embodiments, the probability of random selection of a flow of one oligonucleotide solution following random selection of a flow of a different oligonucleotide solution is greater than the probability of random selection of a flow of one oligonucleotide solution following random selection of a flow of the same oligonucleotide solution.

In various embodiments, an oligonucleotide solution that is selected to be flowed in one cycle could have a smaller probability of being selected to be flowed in the next cycle. For example, for a method which comprises two oligonucleotide solutions, the oligonucleotide solution which was selected in the previous cycle could have a one in four probability of being selected for the next cycle. In which case the oligonucleotide solution which was not selected to be flowed in the previous cycle would have a three in four probability of being selected to be flowed in the next cycle.

In various embodiments, at least one oligonucleotide solution cannot be flowed two cycles in a row. For example, a method comprising two oligonucleotide solutions, one comprising all sixteen oligonucleotide species and one comprising eight oligonucleotide species, one flow of the eight-oligonucleotide species solution is always followed by at least one flow of the sixteen-oligonucleotide species solution.

In various embodiments, more than one oligonucleotide solution can be flowed in the same cycle. For example, in a method comprising two oligonucleotide solutions, each comprising eight oligonucleotide species and together comprising all sixteen oligonucleotide species, both oligonucleotide solutions could be flowed in a single cycle. In such a cycle, all sixteen oligonucleotide species would be flowed. In this way, two different oligonucleotide solutions could make three different oligonucleotide solutions without departing from the scope of these teachings.

In various embodiments, the frequencies of oligonucleotide solution flow can change as sequencing progresses. Numerous frequencies of selection can be applied for a single oligonucleotide solution during a single sequencing run without departing from the scope of these teachings.

FIG. 1 illustrates exemplary amplicons showing leading strand and lagging strand dephasing. The illustration shows a template amplicon 1, an in-phase amplicon 2, a lagging strand dephased amplicon 3 and a leading strand dephased amplicon 4.

Figure 2A:
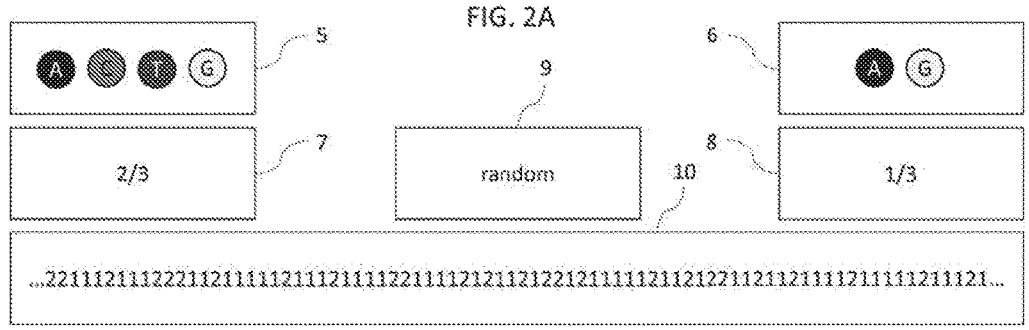
FIG. 2A illustrates an exemplary set of nucleotide solutions and an exemplary order of flow and FIG. 2B illustrates the average of 100 sequencing simulations using those conditions.
Figure 2B:
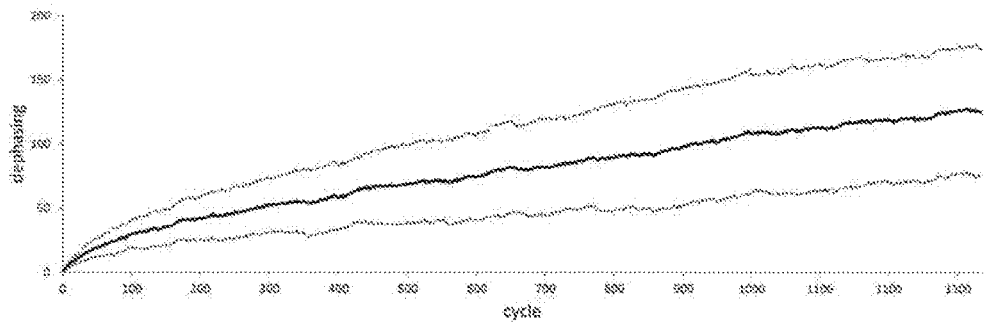

FIG. 2A shows a particular version of the method. In this particular embodiment the method is shown to have two different nucleotide solutions with a first nucleotide solution 5 and a second nucleotide solution 6. Although two different nucleotide solutions are shown here, the method could alternatively comprise three, four, five, six, seven, eight, nine, ten, eleven, twelve, thirteen, fourteen or even fifteen different nucleotide solutions. The first nucleotide solution 5 is shown here to be comprised of four nucleotide species dATP, dTTP, dCTP and dGTP. One, two or three nucleotide species could alternatively be comprised therein. The second nucleotide solution 6 is shown here to be comprised of two nucleotide species dATP and dGTP. One or three nucleotide species could alternatively be comprised therein. Although the second nucleotide solution 6 is shown here to be comprised of the nucleotide species, dATP and dGTP, other combinations of two nucleotide species could be comprised therein. Alternatively, the nucleotide species combinations dATP and dTTP, dATP and dCTP, dTTP and dCTP, dTTP and dGTP or dCTP and dGTP could be used. The average frequency 7 with which the first nucleotide solution 5 is flowed is shown here as two cycles in three cycles. Although the average frequency 7 is shown here to be two cycles in three cycles, this frequency could be any percentage of cycles greater than 0% and less than 100%. The average frequency 8 with which the second nucleotide solution 6 is flowed is shown here as one cycle in three cycles. Although the average frequency 8 is shown here to be one cycle in three cycles, this frequency could be any percentage of cycles greater than 0% and less than 100%. The method of selection 9 of a nucleotide solution 5 or 6 to be flowed in a given cycle is random. This selection could be made using any means of random selection and for any part of the sequencing run or the entire sequencing run. An example order of flow 10 using this embodiment where a flow of the first nucleotide solution 5 is denoted by '1' and a flow of the second nucleotide solution 6 is denoted by '2'. Although a randomly generated example ordering is provided, it is to be understood that the order of flow 10 is for illustration purposes only and not restrictive in any way. FIG. 2B shows a graph of the average dephasing per cycle from 100 sequencing simulations (solid line) plus or minus one standard deviation (dashed lines) using the embodiment illustrated in FIG. 2A for the entire sequencing run. The y axis shows the equivalent amount of dephasing per cycle using the standard method (one nucleotide solution comprising all four nucleotide species flowed in every cycle). The x axis shows the number of cycles. In this particular embodiment the probability of a nucleotide not being incorporated in a cycle is approximately 0.200. On average 1250 cycles are required to sequence 1000 nucleotides. The graph shows that using this method, 1000 nucleotides can be sequenced with the average equivalent dephasing when sequencing approximately 120 nucleotides using the standard method. The simulations were done with the assumption that the rate of dephasing is consistent across the entire sequencing run. The DNA sequences used in the simulations were random, comprising on average equal proportions of each nucleotide species.

Figure 3A:
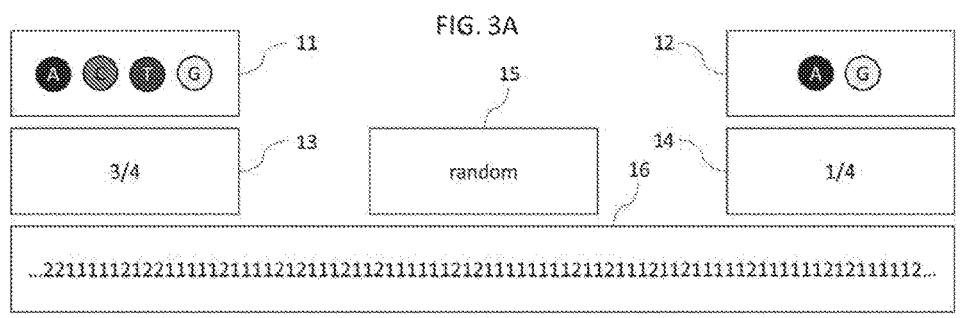
FIG. 3A illustrates another exemplary set of nucleotide solutions and an exemplary order of flow and FIG. 3B illustrates the average of 100 sequencing simulations using those conditions.
Figure 3B:
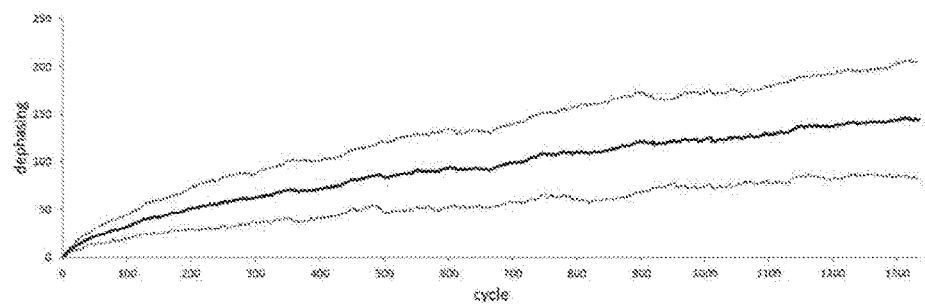

FIG. 3A shows a particular version of the method. In this particular embodiment the method is shown to have two different nucleotide solutions with a first nucleotide solution 11 and a second nucleotide solution 12. The first nucleotide solution 11 is shown here to be comprised of four nucleotide species dATP, dTTP, dCTP and dGTP. The second nucleotide solution 12 is shown here to be comprised of two nucleotide species dATP and dGTP. Although the second nucleotide solution 12 is shown here to be comprised of the nucleotide species, dATP and dGTP, other combinations of two nucleotide species could be comprised therein. Alternatively, the nucleotide species combinations dATP and dTTP, dATP and dCTP, dTTP and dCTP, dTTP and dGTP or dCTP and dGTP could be used. The average frequency 13 with which the first nucleotide solution 11 is flowed is shown here as three cycles in four cycles. The average frequency 14 with which the second nucleotide solution 12 is flowed is shown here as one cycle in four cycles. The method of selection 15 of a nucleotide solution 11 or 12 to be flowed in a given cycle is random. This selection could be made using any means of random selection and for any part of the sequencing run or the entire sequencing run. An example order of flow 16 using this embodiment where a flow of the first nucleotide solution 11 is denoted by '1' and a flow of the second nucleotide solution 12 is denoted by '2'. Although a randomly generated example ordering is provided, it is to be understood that the order of flow 16 is for illustration purposes only and not restrictive in any way. FIG. 3B shows a graph of the average dephasing per cycle from 100 sequencing simulations (solid line) plus or minus one standard deviation (dashed lines) using the embodiment illustrated in FIG. 3A for the entire sequencing run. The y axis shows the equivalent amount of dephasing per cycle using the standard method (one nucleotide solution comprising all four nucleotide species flowed in every cycle). The x axis shows the number of cycles. In this particular embodiment the probability of a nucleotide not being incorporated in a cycle is approximately 0.143. On average 1167 cycles are required to sequence 1000 nucleotides. The graph shows that using this method, 1000 nucleotides can be sequenced with the average equivalent dephasing when sequencing approximately 140 nucleotides using the standard method. The simulations were done with the assumption that the rate of dephasing is consistent across the entire sequencing run. The DNA sequences used in the simulations were random, comprising on average equal proportions of each nucleotide species.

Figure 4A:
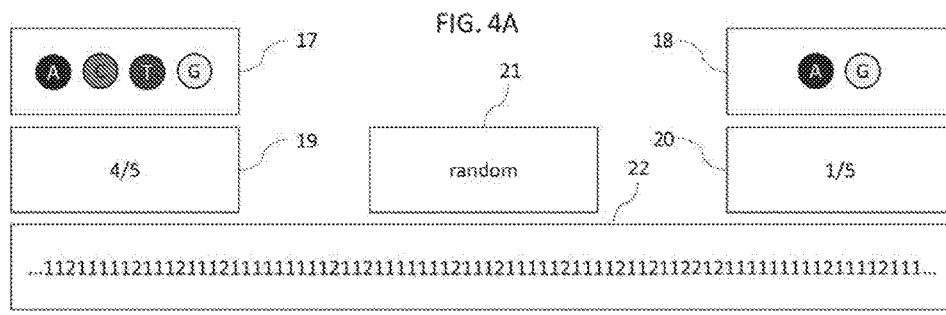
FIG. 4A illustrates another exemplary set of nucleotide solutions and an exemplary order of flow and FIG. 4B illustrates the average of 100 sequencing simulations using those conditions.
Figure 4B:
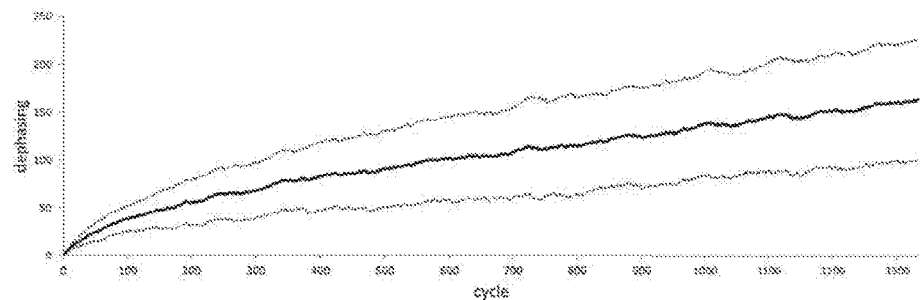

FIG. 4A shows a particular version of the method. In this particular embodiment the method is shown to have two different nucleotide solutions with a first nucleotide solution 17 and a second nucleotide solution 18. The first nucleotide solution 17 is shown here to be comprised of four nucleotide species dATP, dTTP, dCTP and dGTP. The second nucleotide solution 18 is shown here to be comprised of two nucleotide species dATP and dGTP. Although the second nucleotide solution 18 is shown here to be comprised of the nucleotide species, dATP and dGTP, other combinations of two nucleotide species could be comprised therein. Alternatively, the nucleotide species combinations dATP and dTTP, dATP and dCTP, dTTP and dCTP, dTTP and dGTP or dCTP and dGTP could be used. The average frequency 19 with which the first nucleotide solution 17 is flowed is shown here as four cycles in five cycles. The average frequency 20 with which the second nucleotide solution 18 is flowed is shown here as one cycle in five cycles. The method of selection 21 of a nucleotide solution 17 or 18 to be flowed in a given cycle is random. This selection could be made using any means of random selection and for any part of the sequencing run or the entire sequencing run. An example order of flow 22 using this embodiment where a flow of the first nucleotide solution 17 is denoted by '1' and a flow of the second nucleotide solution 18 is denoted by '2'. Although a randomly generated example ordering is provided, it is to be understood that the order of flow 22 is for illustration purposes only and not restrictive in any way. FIG. 4B shows a graph of the average dephasing per cycle from 100 sequencing simulations (solid line) plus or minus one standard deviation (dashed lines) using the embodiment illustrated in FIG. 4A for the entire sequencing run. The y axis shows the equivalent amount of dephasing per cycle using the standard method (one nucleotide solution comprising all four nucleotide species flowed in every cycle). The x axis shows the number of cycles. In this particular embodiment the probability of a nucleotide not being incorporated in a cycle is approximately 0.111. On average 1125 cycles are required to sequence 1000 nucleotides. The graph shows that using this method, 1000 nucleotides can be sequenced with the average equivalent dephasing when sequencing approximately 150 nucleotides using the standard method. The simulations were done with the assumption that the rate of dephasing is consistent across the entire sequencing run. The DNA sequences used in the simulations were random, comprising on average equal proportions of each nucleotide species.

FIG. 5A shows a particular version of the method. In this particular embodiment the method is shown to have two different nucleotide solutions with a first nucleotide solution 23 and a second nucleotide solution 24. Although two different nucleotide solutions are shown here, the method could alternatively comprise three, four, five, six, seven, eight, nine, ten, eleven, twelve, thirteen, fourteen or even fifteen different nucleotide solutions. The first nucleotide solution 23 is shown here to be comprised of four nucleotide species dATP, dTTP, dCTP and dGTP. One, two or three nucleotide species could alternatively be comprised therein. The second nucleotide solution 24 is shown here to be comprised of two nucleotide species dATP and dGTP. One or three nucleotide species could alternatively be comprised therein. Although the second nucleotide solution 24 is shown here to be comprised of the nucleotide species, dATP and dGTP, other combinations of two nucleotide species could be comprised therein. Alternatively, the nucleotide species combinations dATP and dTTP, dATP and dCTP, dTTP and dCTP, dTTP and dGTP or dCTP and dGTP could be used. The average frequency 25 with which the first nucleotide solution 23 is flowed is shown here as four cycles in five cycles. Although the average frequency 25 is shown here to be four cycles in five cycles, this frequency could be any percentage of cycles greater than 0% and less than 100%. The average frequency 26 with which the second nucleotide solution 24 is flowed is shown here as one cycle in five cycles. Although the average frequency 26 is shown here to be one cycle in five cycles, this frequency could be any percentage of cycles greater than 0% and less than 100%. The method of selection 27 of a nucleotide solution 23 or 24 to be flowed in a given cycle is non-random. This non-random selection could be any selection where the nucleotide solution to be flowed is selected by any means other than random selection and for any part of the sequencing run or the entire sequencing run. An order of flow 28 is shown here with a smallest repeating unit of 1, 1, 1, 1, 2, 1, 1, 2, 1, 1, 1, 1, 1, 1, 2, 1, 1, 1, 2, 1, 1, 1, 1, 1, 2 where a flow of the first nucleotide solution 23 is denoted by '1' and a flow of the second nucleotide solution 24 is denoted by '2'. Although a particular smallest repeating unit is shown, any smallest repeating unit which is not an ordering of a single flow of each nucleotide solution could be used. FIG. 5B shows a graph of the average dephasing per cycle from 100 sequencing simulations (solid line) plus or minus one standard deviation (dashed lines) using the embodiment illustrated in FIG. 5A for the entire sequencing run. The y axis shows the equivalent amount of dephasing per cycle using the standard method (one nucleotide solution comprising all four nucleotide species flowed in every cycle). The x axis shows the number of cycles. In this particular embodiment the probability of a nucleotide not being incorporated in a cycle is approximately 0.100. On average 1111 cycles are required to sequence 1000 nucleotides. The graph shows that using this method, 1000 nucleotides can be sequenced with the average equivalent dephasing when sequencing approximately 150 nucleotides using the standard method. The simulations were done with the assumption that the rate of dephasing is consistent across the entire sequencing run. The DNA sequences used in the simulations were random, comprising on average equal proportions of each nucleotide species.

FIG. 6A shows a particular version of the method. In this particular embodiment the method is shown to have two different nucleotide solutions with a first nucleotide solution 29 and a second nucleotide solution 30. The first nucleotide solution 29 is shown here to be comprised of four nucleotide species dATP, dTTP, dCTP and dGTP. The second nucleotide solution 30 is shown here to be comprised of two nucleotide species dATP and dGTP. Although the second nucleotide solution 30 is shown here to be comprised of the nucleotide species, dATP and dGTP, other combinations of two nucleotide species could be comprised therein. Alternatively, the nucleotide species combinations dATP and dTTP, dATP and dCTP, dTTP and dCTP, dTTP and dGTP or dCTP and dGTP could be used. The average frequency 31 with which the first nucleotide solution 29 is flowed is shown here as four cycles in five cycles. The average frequency 32 with which the second nucleotide solution 30 is flowed is shown here as one cycle in five cycles. The method of selection 33 of a nucleotide solution 29 or 30 to be flowed in a given cycle is non-random. An order of flow 34 is shown here with a smallest repeating unit of 1, 1, 1, 1, 2 where a flow of the first nucleotide solution 29 is denoted by '1' and a flow of the second nucleotide solution 30 is denoted by '2'. FIG. 6B shows a graph of the average dephasing per cycle from 100 sequencing simulations (solid line) plus or minus one standard deviation (dashed lines) using the embodiment illustrated in FIG. 6A for the entire sequencing run. The y axis shows the equivalent amount of dephasing per cycle using the standard method (one nucleotide solution comprising all four nucleotide species flowed in every cycle). The x axis shows the number of cycles. In this particular embodiment the probability of a nucleotide not being incorporated in a cycle is approximately 0.100. On average 1111 cycles are required to sequence 1000 nucleotides. The graph shows that using this method, 1000 nucleotides can be sequenced with the average equivalent dephasing when sequencing approximately 240 nucleotides using the standard method. The simulations were done with the assumption that the rate of dephasing is consistent across the entire sequencing run. The DNA sequences used in the simulations were random, comprising on average equal proportions of each nucleotide species.

Figure 7A:
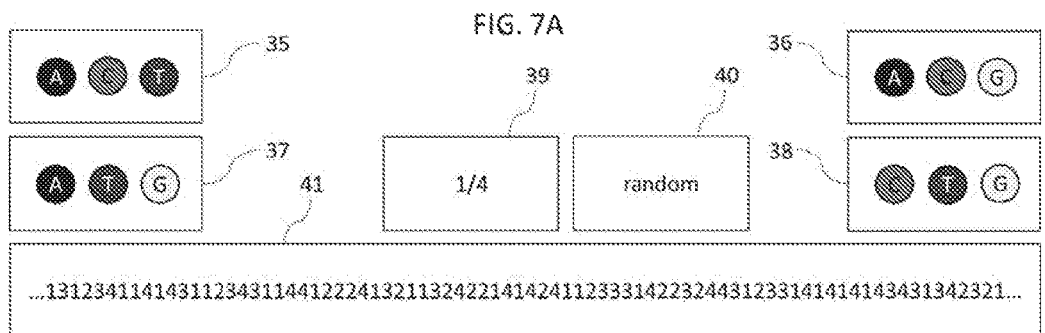
FIG. 7A illustrates another exemplary set of nucleotide solutions and an exemplary order of flow and FIG. 7B illustrates the average of 100 sequencing simulations using those conditions.

FIG. 7A shows a particular version of the method. In this particular embodiment the method is shown to have four different nucleotide solutions with a first nucleotide solution 35, a second nucleotide solution 36, a third nucleotide solution 37 and a fourth nucleotide solution 38. The first nucleotide solution 35 is shown here to be comprised of three nucleotide species dATP, dCTP and dTTP. The second nucleotide solution 36 is shown here to be comprised of three nucleotide species dATP, dCTP and dGTP. The third nucleotide solution 37 is shown here to be comprised of three nucleotide species dATP, dTTP and dGTP. The fourth nucleotide solution 38 is shown here to be comprised of three nucleotide species dCTP, dTTP and dGTP. The average frequency 39 with which the first 35, second 36, third 37 and fourth 38 nucleotide solutions are each flowed is shown here as one cycle in four cycles. The method of selection 40 of a nucleotide solution 35, 36, 37 or 38 to be flowed in a given cycle is random. This selection could be made using any means of random selection and for any part of the sequencing run or the entire sequencing run. An example order of flow 41 using this embodiment where a flow of the first nucleotide solution 35 is denoted by '1' and a flow of the second nucleotide solution 36 is denoted by '2' and a flow of the third nucleotide solution 37 is denoted by '3' and a flow of the fourth nucleotide solution 38 is denoted by '4'. Although a randomly generated example ordering is provided, it is to be understood that the order of flow 41 is for illustration purposes only and not restrictive in any way.

Figure 7B:
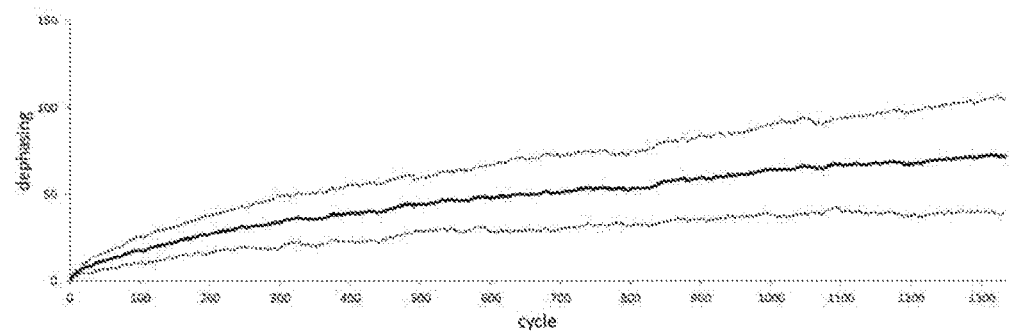

FIG. 7B shows a graph of the average dephasing per cycle from 100 sequencing simulations (solid line) plus or minus one standard deviation (dashed lines) using the embodiment illustrated in FIG. 7A for the entire sequencing run. The y axis shows the equivalent amount of dephasing per cycle using the standard method (one nucleotide solution comprising all four nucleotide species flowed in every cycle). The x axis shows the number of cycles. In this particular embodiment the probability of a nucleotide not being incorporated in a cycle is approximately 0.329. On average 1489 cycles are required to sequence 1000 nucleotides. The graph shows that using this method, 800 nucleotides can be sequenced with the average equivalent dephasing when sequencing approximately 70 nucleotides using the standard method. The simulations were done with the assumption that the rate of dephasing is consistent across the entire sequencing run. The DNA sequences used in the simulations were random, comprising on average equal proportions of each nucleotide species.

FIG. 8A shows a particular version of the method. In this particular embodiment the method is shown to have two different nucleotide solutions with a first nucleotide solution 42 and a second nucleotide solution 43. The first nucleotide solution 42 is shown here to be comprised of three nucleotide species dATP, dCTP and dTTP. Although the first nucleotide solution 42 is shown here to be comprised of the nucleotide species, dATP, dCTP and dTTP, other combinations of three nucleotide species could be comprised therein. Alternatively, the nucleotide species combinations dATP dCTP dGTP, dATP dTTP dGTP or dCTP dTTP dGTP could be used. The second nucleotide solution 43 is shown here to be comprised of three nucleotide species dATP, dCTP and dGTP. Although the second nucleotide solution 43 is shown here to be comprised of the nucleotide species, dATP, dCTP and dGTP, other combinations of three nucleotide species could be comprised therein. Alternatively, the nucleotide species combinations dATP dCTP dTTP, dATP dTTP dGTP or dCTP dTTP dGTP could be used. The average frequency 44 with which the first nucleotide solution 42 is flowed is shown here as one cycle in four cycles when following a flow of the first nucleotide solution 42 or three cycles in four cycles when following a flow of the second nucleotide solution 43. The average frequency 45 with which the second nucleotide solution 43 is flowed is shown here as one cycle in four cycles when following a flow of the second nucleotide solution 43 or three cycles in four cycles when following a flow of the first nucleotide solution 42. The method of selection 46 of a nucleotide solution 42 or 43 to be flowed in a given cycle is random. This selection could be made using any means of random selection and for any part of the sequencing run or the entire sequencing run. An example order of flow 47 using this embodiment where a flow of the first nucleotide solution 42 is denoted by '1' and a flow of the second nucleotide solution 43 is denoted by '2'. Although a randomly generated example ordering is provided, it is to be understood that the order of flow 47 is for illustration purposes only and not restrictive in any way. FIG. 8B shows a graph of the average dephasing per cycle from 100 sequencing simulations (solid line) plus or minus one standard deviation (dashed lines) using the embodiment illustrated in FIG. 8A for the entire sequencing run. The y axis shows the equivalent amount of dephasing per cycle using the standard method (one nucleotide solution comprising all four nucleotide species flowed in every cycle). The x axis shows the number of cycles. In this particular embodiment the probability of a nucleotide not being incorporated in a cycle is approximately 0.329. On average 1489 cycles are required to sequence 1000 nucleotides. The graph shows that using this method, 800 nucleotides can be sequenced with the average equivalent dephasing when sequencing approximately 80 nucleotides using the standard method. The simulations were done with the assumption that the rate of dephasing is consistent across the entire sequencing run. The DNA sequences used in the simulations were random, comprising on average equal proportions of each nucleotide species.

FIG. 9A shows a particular version of the method. In this particular embodiment the method is shown to have two different nucleotide solutions with a first nucleotide solution 48 and a second nucleotide solution 49. The first nucleotide solution 48 is shown here to be comprised of three nucleotide species dATP, dCTP and dTTP. Although the first nucleotide solution 48 is shown here to be comprised of the nucleotide species, dATP, dCTP and dTTP, other combinations of three nucleotide species could be comprised therein. Alternatively, the nucleotide species combinations dATP dCTP dGTP, dATP dTTP dGTP or dCTP dTTP dGTP could be used. The second nucleotide solution 49 is shown here to be comprised of three nucleotide species dATP, dCTP and dGTP. Although the second nucleotide solution 49 is shown here to be comprised of the nucleotide species, dATP, dCTP and dGTP, other combinations of three nucleotide species could be comprised therein. Alternatively, the nucleotide species combinations dATP dCTP dTTP, dATP dTTP dGTP or dCTP dTTP dGTP could be used. The average frequency 50 with which the first nucleotide solution 48 is flowed is shown here as one cycle in two cycles. The average frequency 51 with which the second nucleotide solution 49 is flowed is shown here as one cycle in two cycles. The method of selection 52 of a nucleotide solution 48 or 49 to be flowed in a given cycle is random. This selection could be made using any means of random selection and for any part of the sequencing run or the entire sequencing run. An example order of flow 53 using this embodiment where a flow of the first nucleotide solution 48 is denoted by '1' and a flow of the second nucleotide solution 49 is denoted by '2'. Although a randomly generated example ordering is provided, it is to be understood that the order of flow 53 is for illustration purposes only and not restrictive in any way. FIG. 9B shows a graph of the average dephasing per cycle from 100 sequencing simulations (solid line) plus or minus one standard deviation (dashed lines) using the embodiment illustrated in FIG. 9A for the entire sequencing run. The y axis shows the equivalent amount of dephasing per cycle using the standard method (one nucleotide solution comprising all four nucleotide species flowed in every cycle). The x axis shows the number of cycles. In this particular embodiment the probability of a nucleotide not being incorporated in a cycle is approximately 0.469. On average 1883 cycles are required to sequence 1000 nucleotides. The graph shows that using this method, 700 nucleotides can be sequenced with the average equivalent dephasing when sequencing approximately 55 nucleotides using the standard method. The simulations were done with the assumption that the rate of dephasing is consistent across the entire sequencing run. The DNA sequences used in the simulations were random, comprising on average equal proportions of each nucleotide species.

Figure 10B:
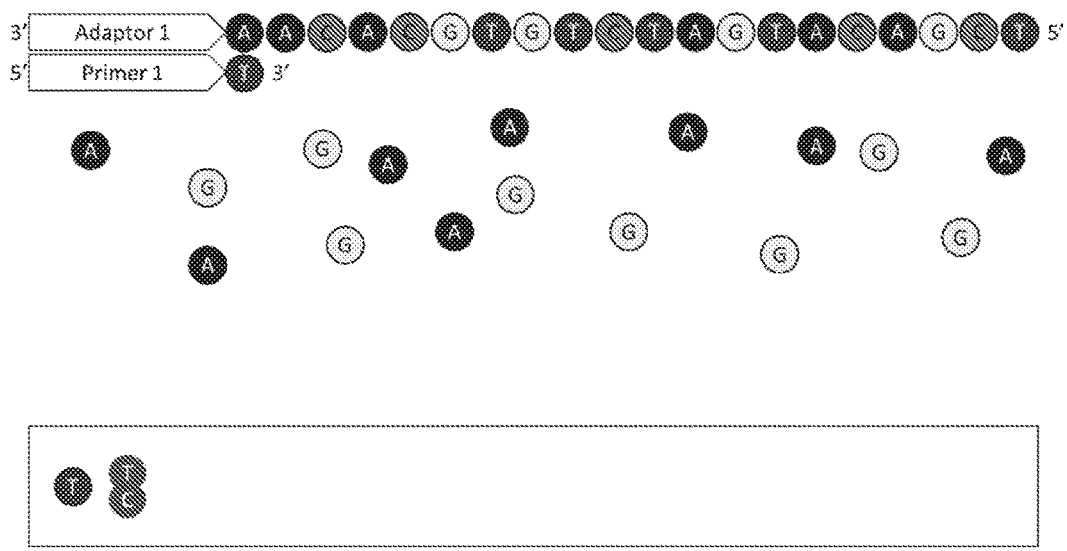
FIG. 10A-10Q illustrate schematically a series of flows using an embodiment of the method described herein, demonstrating the addition of nucleotides to the growing amplicon and a representation of the fluorescent signal from each flow.
Figure 10C:
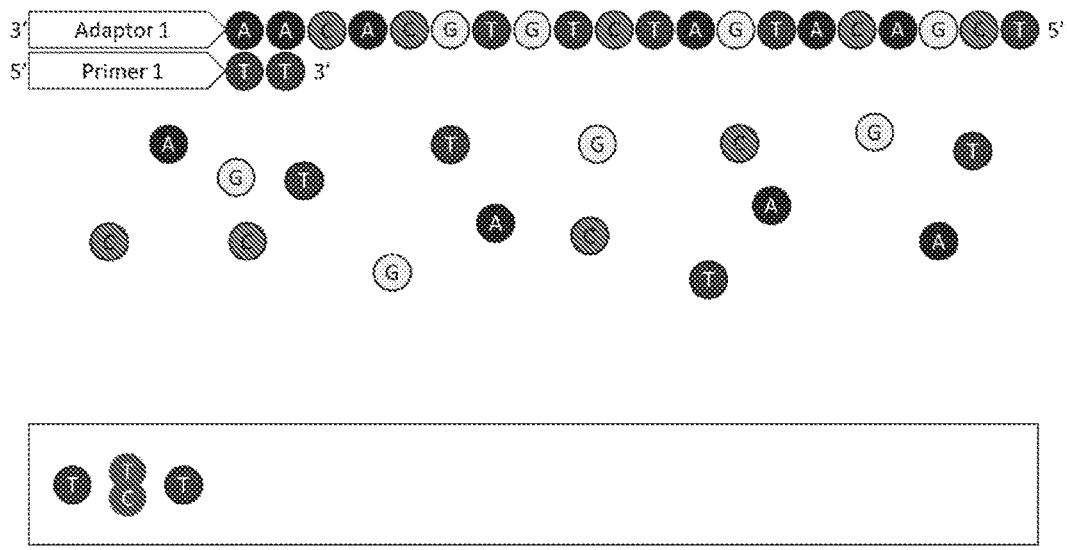
Figure 10D:
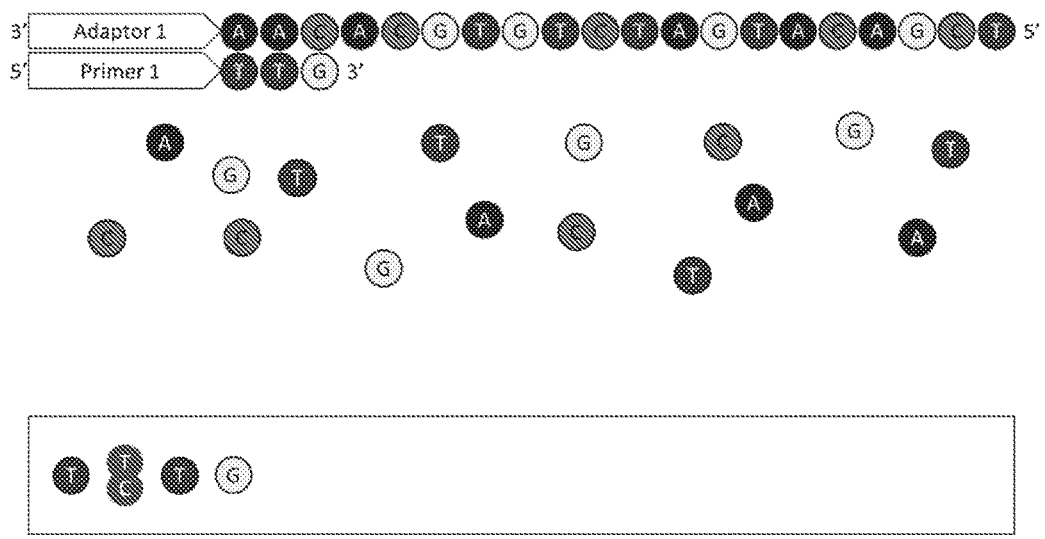
Figure 10E:
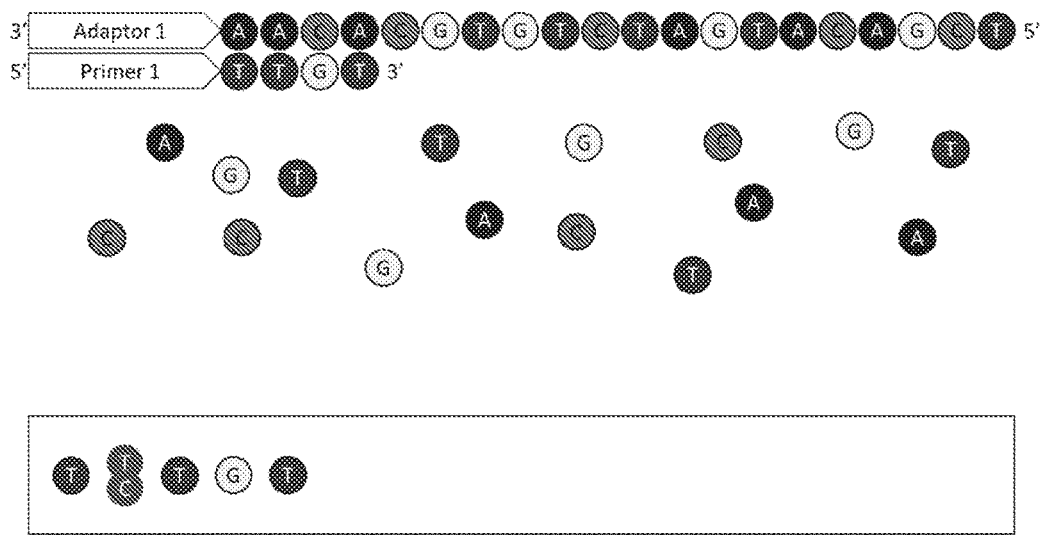
Figure 10H:
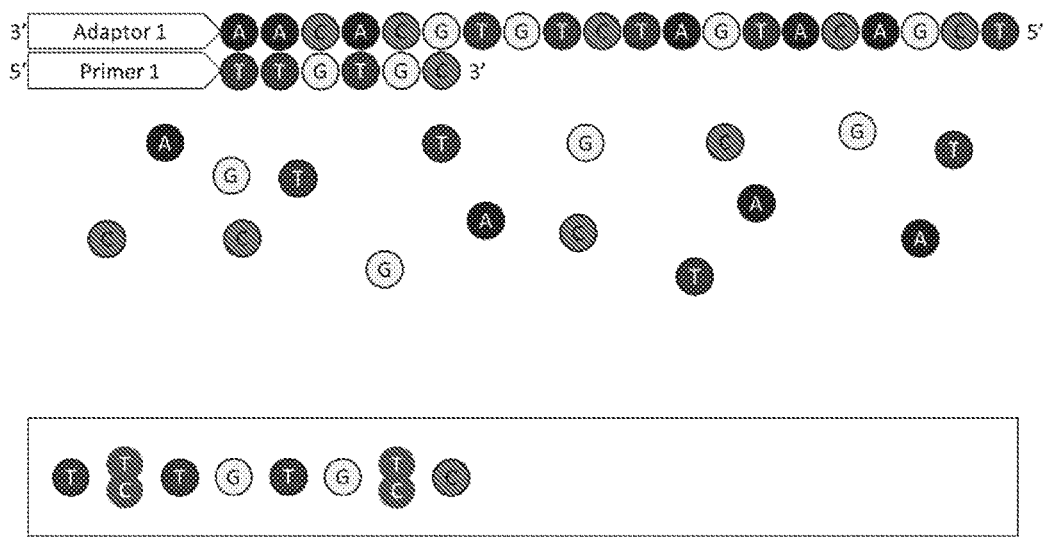
Figure 10I:
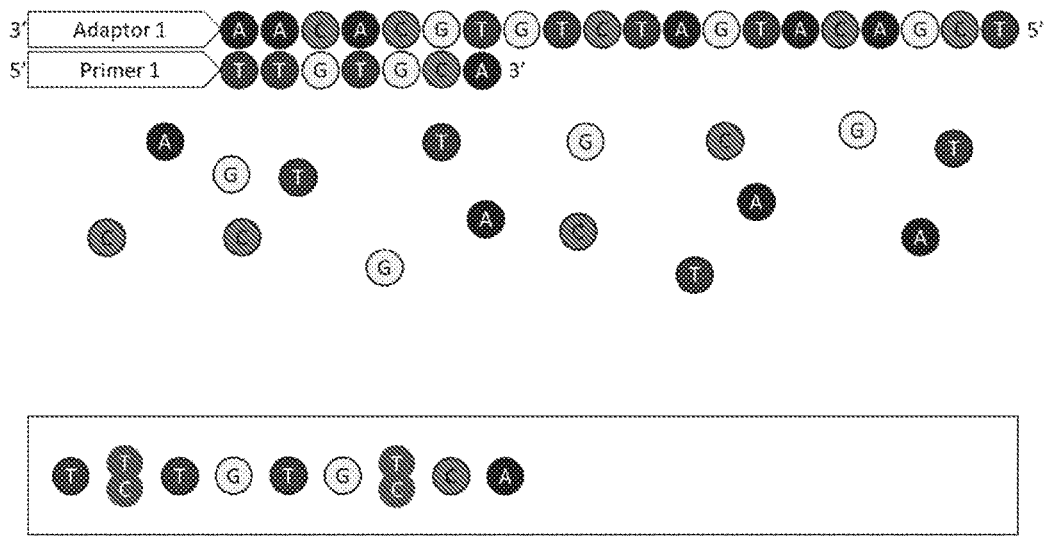
Figure 10J:
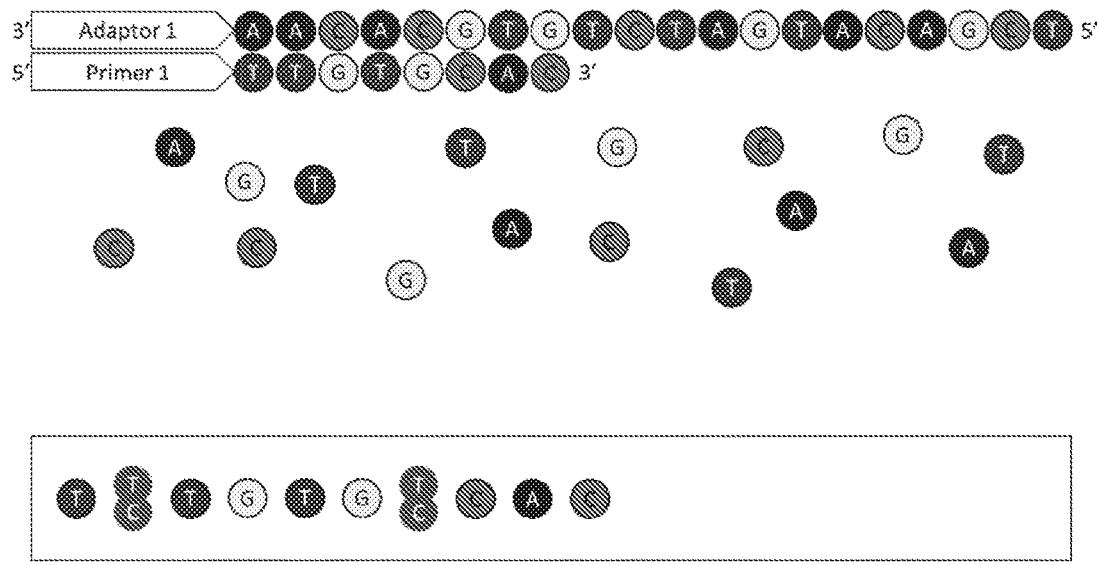
Figure 10K:
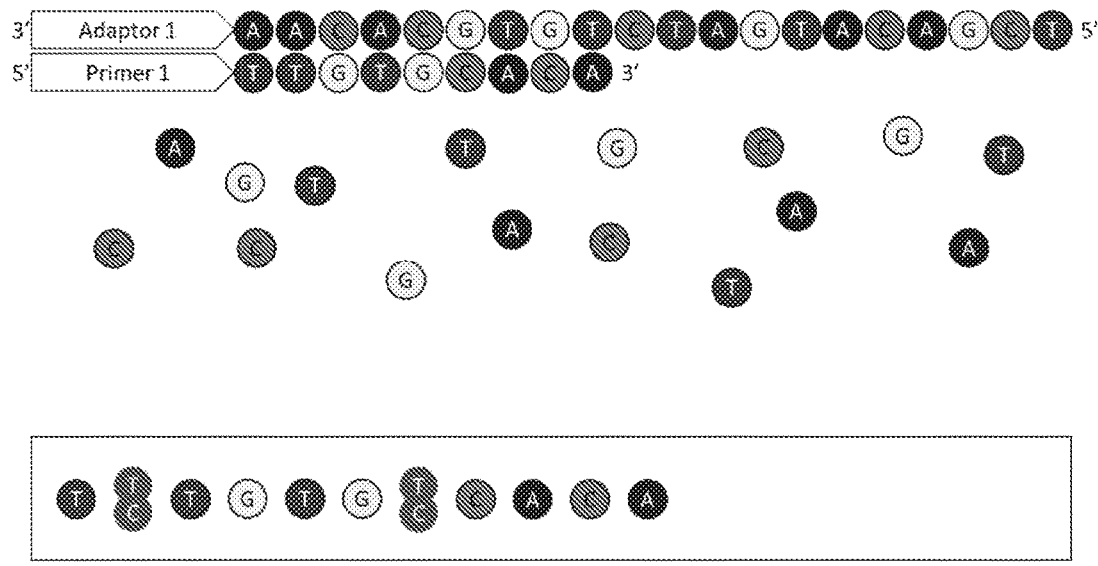
Figure 10L:
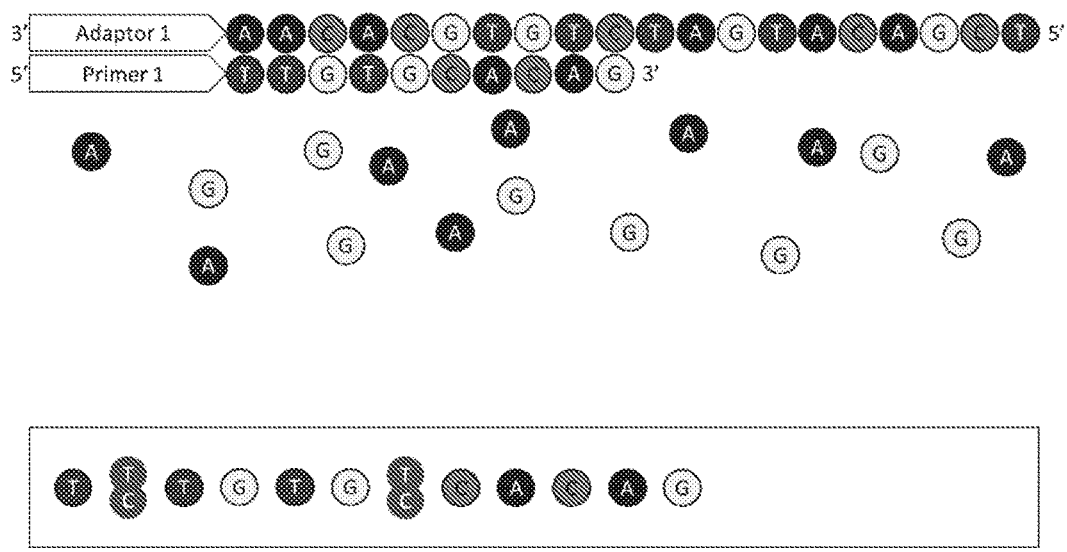
Figure 10M:
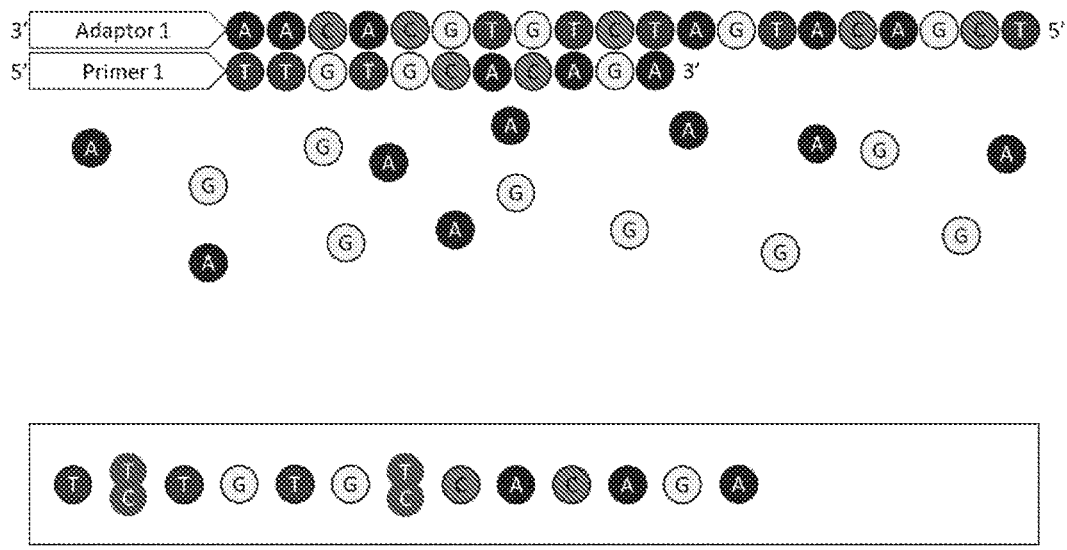
Figure 10N:
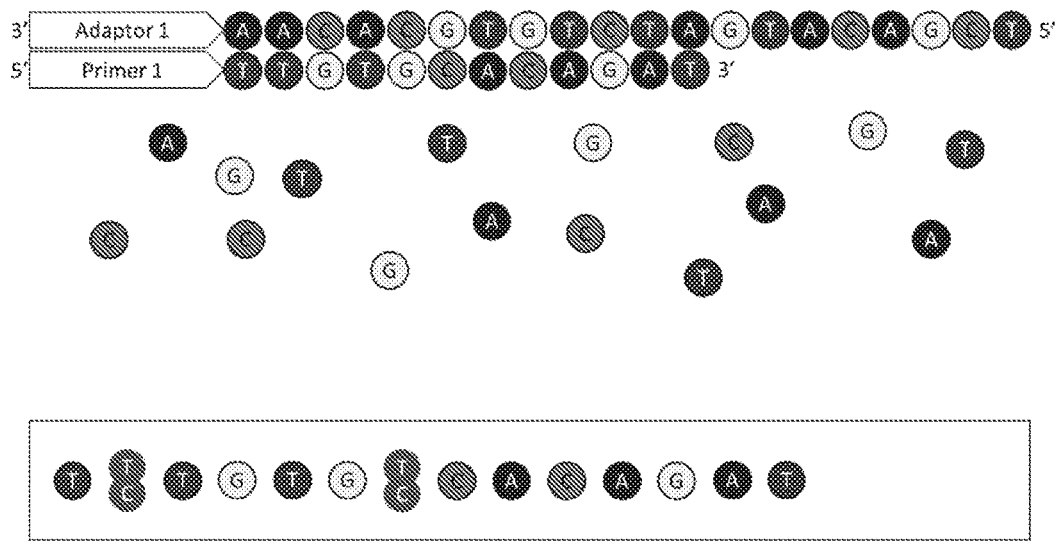
Figure 10O:
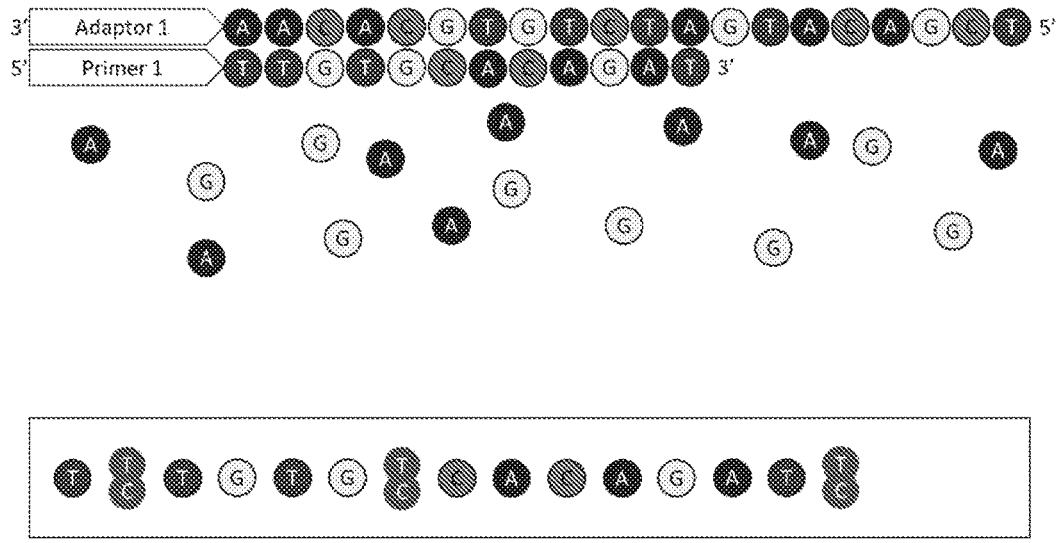
Figure 10P:
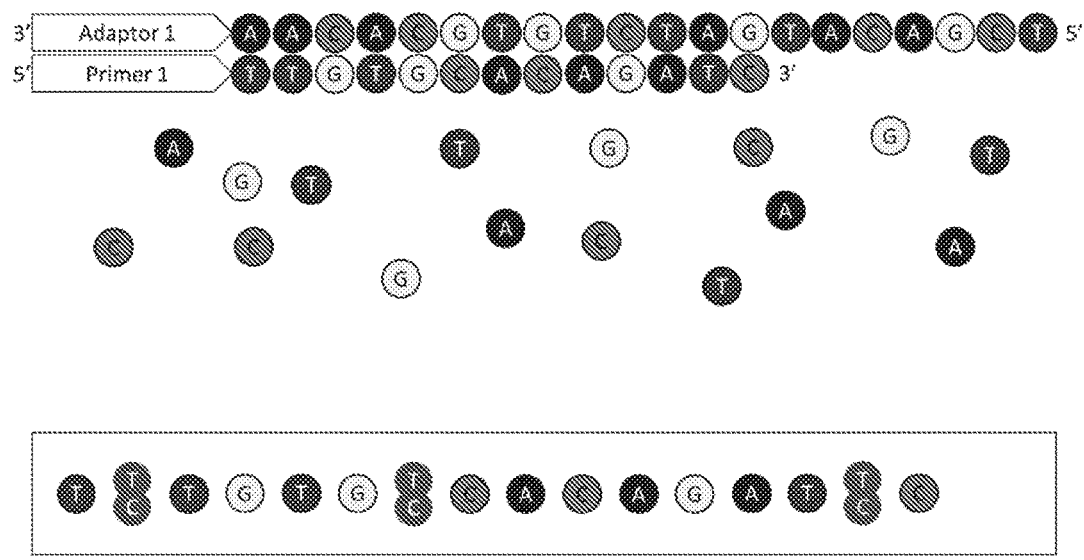
Figure 10Q:
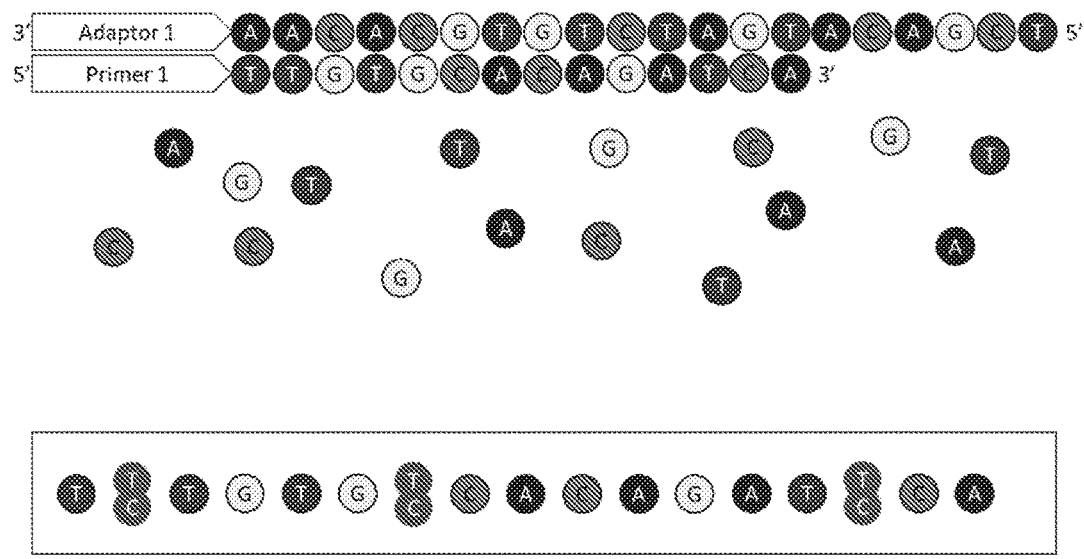

FIG. 10A-10Q illustrate schematically a series of flows using an embodiment of the method described herein, demonstrating the addition of nucleotides to the growing amplicon 54 with each nucleotide solution flow 55 and a representation of the fluorescent signal for each flow 56 showing which nucleotide species, if any, was incorporated. The nucleotide representations without black boarders show the predicted nucleotide species to be incorporated next in the sequence. When no nucleotide species is incorporated in the growing amplicon, there is no fluorescent signal which indicates the next nucleotide species to be incorporated will be one of the nucleotide species not included in that flow.

Figure 11A:
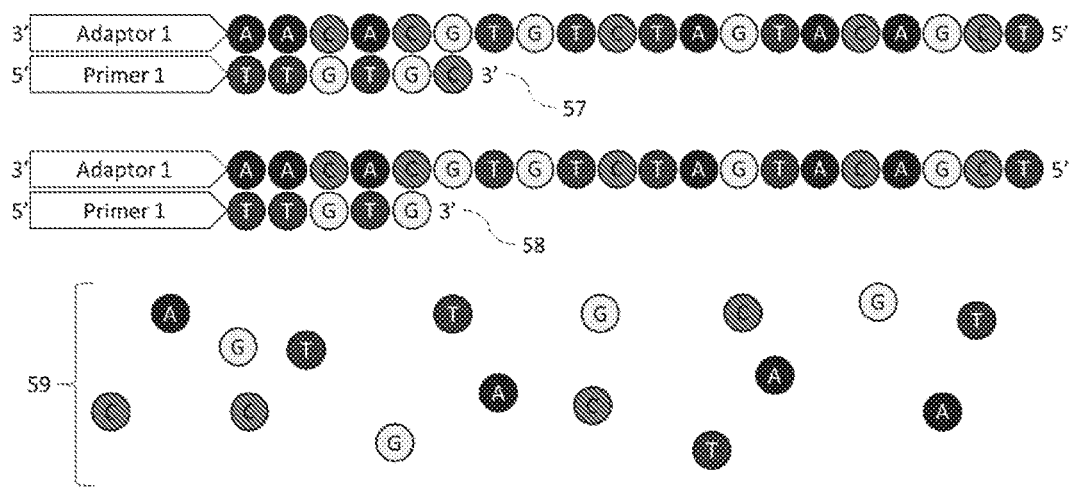
Figure 11B:
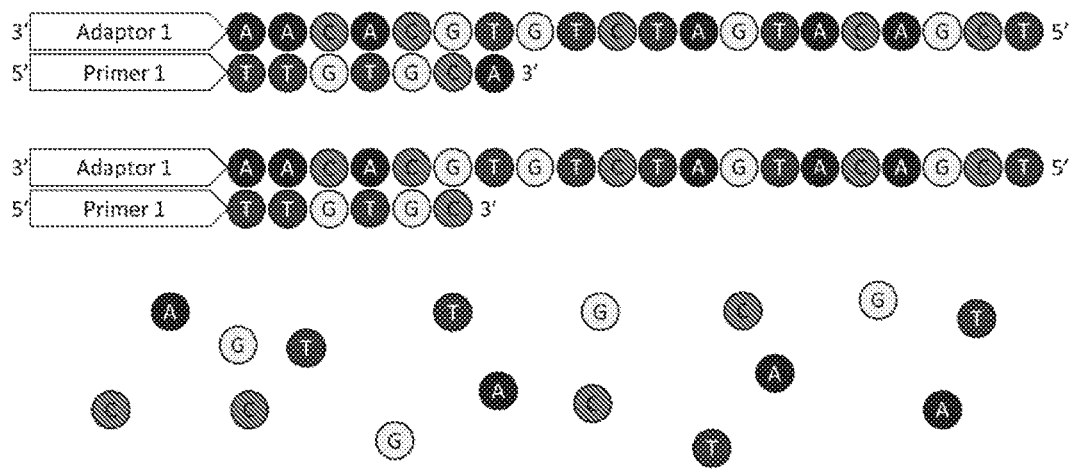

FIG. 11A-11C illustrate schematically an example of how an embodiment of the method described herein, can resynchronise out-of-phase amplicons. An in-phase amplicon 57 and a lagging strand dephased amplicon 58 are exposed to flows of nucleotide solutions 59. In this illustration, when a nucleotide species is added to the lagging strand dephased amplicon 58, but not the in-phase amplicon 57, the lagging strand dephased amplicon 58 becomes in-phase.

FIG. 12A shows a particular version of the method. In this particular embodiment the method is shown to have two different oligonucleotide solutions with a first oligonucleotide solution 60 and a second oligonucleotide solution 61. Although two different oligonucleotide solutions are shown here, the method could alternatively comprise more than two oligonucleotide solutions. The first oligonucleotide solution 60 is shown here to be comprised of eight oligonucleotide species. Although eight oligonucleotide species are shown here, the first oligonucleotide solution 60 could comprise one to sixteen oligonucleotide species. The second oligonucleotide solution 61 is shown here to be comprised of eight oligonucleotide species. Although eight oligonucleotide species are shown here, the second oligonucleotide solution 61 could comprise one to fifteen oligonucleotide species. The average frequency 62 with which the first oligonucleotide solution 60 is flowed is shown here as one cycle in two cycles. Although the average frequency 62 is shown here to be one cycle in two cycles, this frequency could be any percentage of cycles greater than 0% and less than 100%. The average frequency 63 with which the second oligonucleotide solution 61 is flowed is shown here as one cycle in two cycles. Although the average frequency 63 is shown here to be one cycle in two cycles, this frequency could be any percentage of cycles greater than 0% and less than 100%. The method of selection 64 of an oligonucleotide solution 60 or 61 to be flowed in a given cycle is shown here to be random. Although the method of selection 64 is shown here to be random, non-random selection could also be used. This selection could be made using any means of random selection and for any part of the sequencing run or the entire sequencing run. An example order of flow 65 using this embodiment where a flow of the first oligonucleotide solution 60 is denoted by '1' and a flow of the second oligonucleotide solution 61 is denoted by '2'. Although a randomly generated example ordering is provided, it is to be understood that the order of flow 65 is for illustration purposes only and not restrictive in any way. FIG. 12B shows a graph of the average dephasing per cycle from 100 sequencing simulations (solid line) plus or minus one standard deviation (dashed lines) using the embodiment illustrated in FIG. 12A for the entire sequencing run. The y axis shows the equivalent amount of dephasing per cycle using the standard method (one oligonucleotide solution comprising all sixteen oligonucleotide species flowed in every cycle). The x axis shows the number of cycles. In this particular embodiment the probability of a nucleotide not being incorporated in a cycle is approximately 0.500. On average 2000 cycles are required for the equivalent sequencing of 1000 cycles using the standard method. The graph shows that using this method, the equivalent of 600 cycles of sequencing can be done with the average equivalent dephasing as approximately 40 sequencing cycles using the standard method.

The simulations were done with the assumption that the rate of dephasing is consistent across the entire sequencing run. The DNA sequences used in the simulations were random, comprising on average equal proportions of each nucleotide species.

Figure 13A:
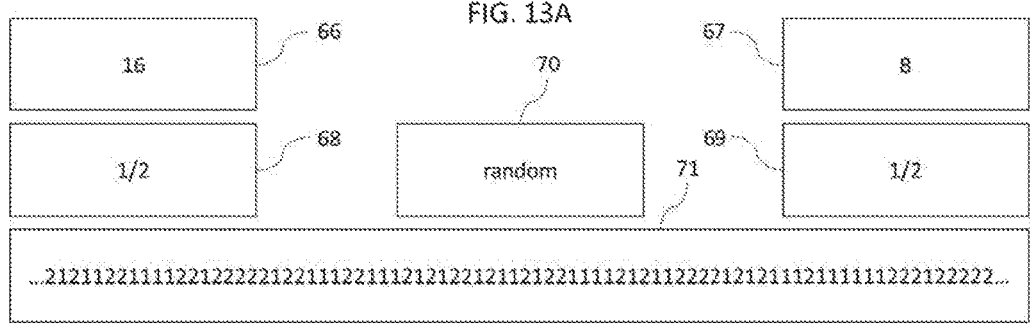
FIG. 13A illustrates another exemplary set of oligonucleotide solutions and an exemplary order of flow and FIG. 13B illustrates the average of 100 sequencing simulations using those conditions.
Figure 13B:
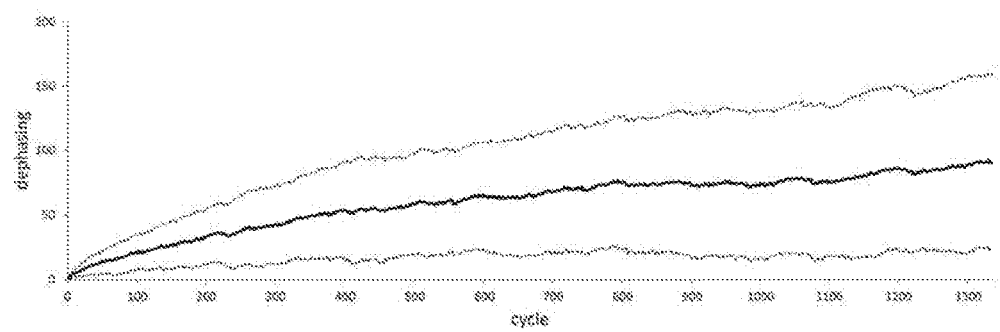

FIG. 13A shows a particular version of the method. In this particular embodiment the method is shown to have two different oligonucleotide solutions with a first oligonucleotide solution 66 and a second oligonucleotide solution 67. The first oligonucleotide solution 66 is shown here to be comprised of sixteen oligonucleotide species. The second oligonucleotide solution 67 is shown here to be comprised of eight oligonucleotide species. The average frequency 68 with which the first oligonucleotide solution 66 is flowed is shown here as one cycle in two cycles. The average frequency 69 with which the second oligonucleotide solution 67 is flowed is shown here as one cycle in two cycles. The method of selection 70 of an oligonucleotide solution 66 or 67 to be flowed in a given cycle is random. This selection could be made using any means of random selection and for any part of the sequencing run or the entire sequencing run. An example order of flow 71 using this embodiment where a flow of the first oligonucleotide solution 66 is denoted by '1' and a flow of the second oligonucleotide solution 67 is denoted by '2'. Although a randomly generated example ordering is provided, it is to be understood that the order of flow 71 is for illustration purposes only and not restrictive in any way. FIG. 13B shows a graph of the average dephasing per cycle from 100 sequencing simulations (solid line) plus or minus one standard deviation (dashed lines) using the embodiment illustrated in FIG. 13A for the entire sequencing run. The y axis shows the equivalent amount of dephasing per cycle using the standard method (one oligonucleotide solution comprising all sixteen oligonucleotide species flowed in every cycle). The x axis shows the number of cycles. In this particular embodiment the probability of a nucleotide not being incorporated in a cycle is approximately 0.333. On average 1500 cycles are required for the equivalent sequencing of 1000 cycles using the standard method. The graph shows that using this method, the equivalent of 600 cycles of sequencing can be done with the average equivalent dephasing as approximately 70 sequencing cycles using the standard method. The simulations were done with the assumption that the rate of dephasing is consistent across the entire sequencing run. The DNA sequences used in the simulations were random, comprising on average equal proportions of each nucleotide species.

Although the invention has been explained in relation to its preferred embodiments, it is to be understood that many other possible modifications and variations can be made without departing from the spirit and scope of the invention.

The invention claimed is:

1. A method for nucleic acid sequencing, comprising:
exposing a plurality of clusters of a plurality of template polynucleotide strands with a sequencing primer and a polymerase enzyme operably bound therewith to a series of flows of a plurality of nucleotide solutions, wherein the nucleotide solutions are flowed in an order of flow which is not a continuous repeat of an ordering of a single flow of each of the nucleotide solutions; and
obtaining a fluorescence signal indicative of which, if any, nucleotide species incorporated to determine a predicted sequence of nucleotides corresponding to the template polynucleotide strands.

2. The method of claim 1 wherein the plurality of nucleotide solutions is comprised of two different said nucleotide solutions which together are comprised of all four nucleotide species.

3. The method of claim 2 wherein one of the nucleotide solutions is comprised of 2-4 nucleotide species and the other one of the nucleotide solutions is comprised of 1-3 nucleotide species.

4. The method of claim 1 wherein the plurality of nucleotide solutions is comprised of three different said nucleotide solutions which together are comprised of all four nucleotide species.

5. The method of claim 4 wherein one of the nucleotide solutions is comprised of 2-4 nucleotide species and the other two said nucleotide solutions are each comprised of 1-3 nucleotide species.

6. The method of claim 1 wherein the plurality of nucleotide solutions is comprised of four different said nucleotide solutions which together are comprised of all four nucleotide species.

7. The method of claim 6 wherein one of the nucleotide solutions is comprised of 1-4 nucleotide species and the other three said nucleotide solutions are each comprised of 1-3 nucleotide species.

8. The method of claim 1 wherein the plurality of nucleotide solutions is comprised of at least five different said nucleotide solutions which together are comprised of all four nucleotide species.

9. The method of claim 8 wherein one of the nucleotide solutions is comprised of 2-4 nucleotide species and the other said nucleotide solutions are each comprised of 1-3 nucleotide species.

10. The method of claim 1 wherein the order of flow is at least in part a repeat of an ordering of the nucleotide solutions with a minimum repeating unit which is greater than a single flow of each of the nucleotide solutions.

11. The method of claim 10 wherein the minimum repeating unit is equally comprised of each of the nucleotide solutions.

12. The method of claim 10 wherein the minimum repeating unit is not equally comprised of each of the nucleotide solutions.

13. The method of claim 1 wherein the order of flow is at least in part a random ordering of the nucleotide solutions.

14. The method of claim 13 wherein the random ordering is an ordering in which each of the nucleotide solutions have equal probabilities of being flowed in a given cycle.

15. The method of claim 13 wherein the random ordering is an ordering in which at least two of the nucleotide solutions have unequal probabilities of being flowed in a given cycle.

16. The method of claim 15 wherein there is a smaller probability of a flow of one of the nucleotide solutions being followed by a flow of the same kind than by a flow of a different one of the nucleotide solutions.

17. The method of claim 1 wherein the order of flow comprises at least one cycle in which at least two of the nucleotide solutions are flowed.

18. A method for nucleic acid sequencing, comprising:
exposing a plurality of clusters of a plurality of template polynucleotide strands with a sequencing primer operably bound therewith to a series of flows of a plurality of oligonucleotide solutions,
wherein the oligonucleotide solutions are flowed in an order of flow which is not a continuous repeat of an ordering of a single flow of each of the oligonucleotide solutions; and
obtaining a fluorescence signal indicative of which, if any, oligonucleotide species incorporated to determine a predicted sequence of nucleotides corresponding to the template polynucleotide strands.

19. The method of claim 18 wherein the plurality of oligonucleotide solutions is comprised of at least two different said oligonucleotide solutions which together are comprised of all sixteen oligonucleotide species, with 3' nucleotides AA, AT, AC, AG, TA, TT, TC, TG, CA, CT, CC, CG, GA, GT, GC and GG.

20. The method of claim 19 wherein one of the oligonucleotide solutions is comprised of 1-16 oligonucleotide species and the other said oligonucleotide solutions are each comprised of 1-15 oligonucleotide species.

21. The method of claim 18 wherein the order of flow is at least in part a repeat of an ordering of the oligonucleotide solutions with a minimum repeating unit which is greater than a single flow of each of the oligonucleotide solutions.

22. The method of claim 21 wherein the minimum repeating unit is equally comprised of each of the oligonucleotide solutions.

23. The method of claim 21 wherein the minimum repeating unit is not equally comprised of each of the oligonucleotide solutions.

24. The method of claim 18 wherein the order of flow is at least in part a random ordering of the oligonucleotide solutions.

25. The method of claim 24 wherein the random ordering is an ordering in which each of the oligonucleotide solutions have equal probabilities of being flowed in a given cycle.

26. The method of claim 24 wherein the random ordering is an ordering in which at least two of the oligonucleotide solutions have unequal probabilities of being flowed in a given cycle.

27. The method of claim 26 wherein there is a smaller probability of a flow of one of the oligonucleotide solutions being followed by a flow of the same kind than by a flow of a different one of the oligonucleotide solutions.

28. The method of claim 18 wherein the order of flow comprises at least one cycle in which at least two of the oligonucleotide solutions are flowed.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Randomly generated sequence

<400> SEQUENCE: 1
tcgacatgat ctgtgcacaa                                          20

<210> SEQ ID NO 2
<211> LENGTH: 13
<212> TYPE: DNA
<213> ORGANISM: Artificial Sequence
<220> FEATURE:
<223> OTHER INFORMATION: Randomly generated sequence
```

```
<400> SEQUENCE: 2
ttgtgcacag atc                                                              13

<210> SEQ ID NO 3
<211> LENGTH: 12
<212> TYPE: DNA
<213> ORGANISM: Artificial Sequence
<220> FEATURE:
<223> OTHER INFORMATION: Randomly generated sequence

<400> SEQUENCE: 3
ttgtgcacag at                                                               12

<210> SEQ ID NO 4
<211> LENGTH: 14
<212> TYPE: DNA
<213> ORGANISM: Artificial Sequence
<220> FEATURE:
<223> OTHER INFORMATION: Randomly generated sequence

<400> SEQUENCE: 4
ttgtgcacag atca                                                             14

<210> SEQ ID NO 5
<211> LENGTH: 10
<212> TYPE: DNA
<213> ORGANISM: Artificial Sequence
<220> FEATURE:
<223> OTHER INFORMATION: Randomly generated sequence

<400> SEQUENCE: 5
ttgtgcacag                                                                  10

<210> SEQ ID NO 6
<211> LENGTH: 11
<212> TYPE: DNA
<213> ORGANISM: Artificial Sequence
<220> FEATURE:
<223> OTHER INFORMATION: Randomly generated sequence

<400> SEQUENCE: 6
ttgtgcacag a                                                                11
```